US011639325B2

United States Patent
Tsai et al.

(10) Patent No.: US 11,639,325 B2
(45) Date of Patent: *May 2, 2023

(54) COMPOSITIONS OF POLYHYDROXYLATED BENZOPHENONES AND METHODS OF TREATMENT OF NEURODEGENERATIVE DISORDERS

(71) Applicants: Massachusetts Institute of Technology, Cambridge, MA (US); The General Hospital Corporation, Boston, MA (US)

(72) Inventors: Li-Huei Tsai, Cambridge, MA (US); Stephen J. Haggarty, Gloucester, MA (US); Debasis Patnaik, Weymouth, MA (US); Ping-Chieh Pao, Cambridge, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/116,427

(22) Filed: Dec. 9, 2020

(65) Prior Publication Data

US 2021/0171429 A1 Jun. 10, 2021

Related U.S. Application Data

(63) Continuation of application No. 16/010,030, filed on Jun. 15, 2018, now Pat. No. 11,180,438, which is a continuation of application No. PCT/US2016/067592, filed on Dec. 19, 2016.

(60) Provisional application No. 62/268,899, filed on Dec. 17, 2015.

(51) Int. Cl.
| | | |
|---|---|---|
| C07C 49/83 | (2006.01) | |
| A61K 9/00 | (2006.01) | |
| A61K 45/06 | (2006.01) | |
| A61K 31/12 | (2006.01) | |
| C07C 49/84 | (2006.01) | |
| C07C 215/20 | (2006.01) | |
| C07C 69/017 | (2006.01) | |
| A61P 25/28 | (2006.01) | |
| C07C 65/34 | (2006.01) | |

(52) U.S. Cl.
CPC .......... *C07C 49/83* (2013.01); *A61K 9/0019* (2013.01); *A61K 9/0043* (2013.01); *A61K 9/0053* (2013.01); *A61K 31/12* (2013.01); *A61K 45/06* (2013.01); *A61P 25/28* (2018.01); *C07C 49/84* (2013.01); *C07C 65/34* (2013.01); *C07C 69/017* (2013.01); *C07C 215/20* (2013.01)

(58) Field of Classification Search
None
See application file for complete search history.

(56) References Cited

U.S. PATENT DOCUMENTS

| | | | |
|---|---|---|---|
| 4,015,017 | A | 3/1977 | Gazave et al. |
| 5,262,564 | A | 11/1993 | Kun et al. |
| 2010/0075926 | A1 | 3/2010 | Tsai et al. |
| 2013/0096129 | A1 | 4/2013 | Tsai et al. |
| 2014/0080800 | A1 | 3/2014 | Holson et al. |

FOREIGN PATENT DOCUMENTS

| | | |
|---|---|---|
| WO | WO 2001/049281 A2 | 7/2001 |
| WO | WO 2001/081288 A1 | 11/2001 |

OTHER PUBLICATIONS

International Search Report and Written Opinion for PCT/US2016/067592, dated Feb. 17, 2017.
International Preliminary Report on Patentability for PCT/US2016/067592, dated Jun. 19, 2018.
Baruch et al., PD-1 immune checkpoint blockade reduces pathology and improves memory in mouse models of Alzheimer's disease. Nat Med. Feb. 2016;22(2):135-7. doi: 10.1038/nm.4022. Epub Jan. 18, 2016.
Cruz et al., Aberrant Cdk5 activation by p25 triggers pathological events leading to neurodegeneration and neurofibrillary tangles. Neuron. Oct. 30, 2003;40(3):471-83.
Fries et al., Über Homologe des Cumaranons und ihre Abkömmlinge. Chem Ber. 1908;41(3):4271-4284. doi: 10.1002/cber.190804103146.
Porsolt et al., Antagonism by exifone, a new cognitive enhancing agent, of the amnesias induced by four benzodiazepines in mice. Psychopharmacology (Berl). 1988;95(3):291-7.
Rye et al., Advances in label-free screening approaches for studying histone acetyltransferases. J Biomol Screen. Dec. 2011;16(10):1186-95. doi: 10.1177/1087057111418653. Epub Sep. 9, 2011.
Rye et al., Advances in label-free screening approaches for studying sirtuin-mediated deacetylation. J Biomol Screen. Dec. 2011;16(10):1217-26. doi: 10.1177/1087057111420291. Epub Sep. 12, 2011.
Silva et al., Human iPSC-Derived Neuronal Model of Tau-A152T Frontotemporal Dementia Reveals Tau-Mediated Mechanisms of Neuronal Vulnerability. Stem Cell Reports. Sep. 13, 2016;7(3):325-340. doi: 10.1016/j.stemcr.2016.08.001. Epub Sep. 1, 2016.

*Primary Examiner* — Samantha L Shterengarts
(74) *Attorney, Agent, or Firm* — Wolf, Greenfield & Sacks, P.C.

(57) ABSTRACT

The present invention relates to polyhydroxylated benzophenone compounds useful in the treatment of neurodegenerative, neurological, psychiatric, and cognitive diseases, in particular those associated with a deficiency in HDAC1 deacetylase activity.

42 Claims, 16 Drawing Sheets

FIG. 3A
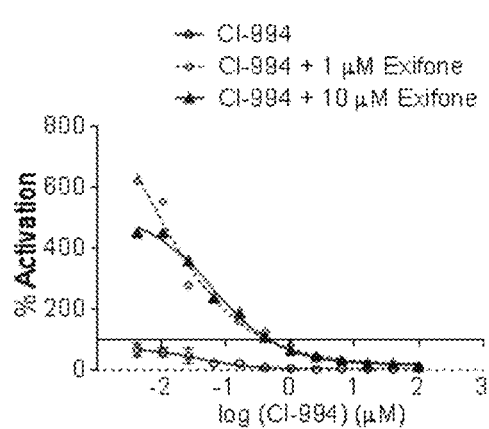
FIG. 3B
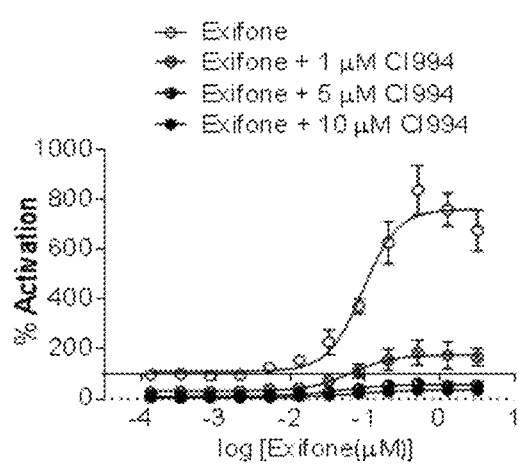
FIG. 3C
Best-fit values determined from sigmoidal dose-response (variable slope) of Fig. 3B
|  | exifone | exifone + 1 µM CI-994 | exifone + 5 µM CI-994 | exifone + 10 µM CI-994 |
|---|---|---|---|---|
| Bottom | 111 | 31.24 | 11.61 | 4.932 |
| Top | 760.3 | 177.9 | 58.01 | 36.36 |
| HillSlope | 1.87 | 1.53 | 1.43 | 1.17 |
| $EC_{50}$ (µM) | 0.093 | 0.065 | 0.047 | 0.069 |

Enriched GO terms from Anti-PD-1_UP & Exifone_UP

| Pathway name | Entities pValue |
|---|---|
| Interferon Signaling | 3.48E-08 |
| MHC class II antigen presentation | 5.41E-08 |
| Interferon gamma signaling | 3.86E-07 |

COMPOSITIONS OF POLYHYDROXYLATED BENZOPHENONES AND METHODS OF TREATMENT OF NEURODEGENERATIVE DISORDERS

CROSS-REFERENCE TO RELATED APPLICATIONS

This application is a is a continuation of U.S. application Ser. No. 16/010,030, filed Jun. 15, 2018, entitled "Compositions of Polyhydroxylated Benzophenones and Methods of Treatment of Neurodegenerative Disorders", which is continuation of International Patent Application No. PCT/US2016/067592, filed Dec. 19, 2016, entitled "Compositions of Polyhydroxylated Benzophenones and Methods of Treatment of Neurodegenerative Disorders," which claims priority to U.S. Provisional Application No. 62/268,899, filed Dec. 17, 2015, each of which is incorporated herein by reference in its entirety for all purposes.

FIELD OF THE INVENTION

The present invention provides treatments of neurodegeneration, neurological disorders, psychiatric disorders, and cognitive deficits. In particular, polyhydroxylated benzophenones are described for their use in these treatments.

BACKGROUND OF THE INVENTION

Recent work has focused on identifying and characterizing small molecule activators of histone deacetylase (HDAC) 1 as a novel strategy for preventing neurodegeneration by blocking cell cycle re-entry & DNA damage in Alzheimer's disease (AD) (Tsai et al. 2013). Deregulation of HDAC1 activity is critically involved central nervous system pathology that may be significant to stroke/ischemia and AD (Kim et al. 2008). Inhibition of the histone deacetylase HDAC1 catalytic activity by p25/Cdk5 in an inducible p25/Cdk5 neurodegeneration mouse model resulted in development of key pathological hallmarks of AD, including neuronal loss in the forebrain, increased β-amyloid peptide production. Also, in a rodent stroke model, HDAC1 overexpression resulted in a rescue against p25-induced DNA damage and neuronal death thus demonstrating therapeutic potential for HDAC1 gain-of-function as neuroprotective. These results indicated a role for HDAC1 in the maintenance of DNA integrity and cell cycle suppression in neurons (Kim et al. 2008). Therefore there is a need for methods for activating HDAC1, specifically increasing its ability to deacetylate proteins through its enzymatic activity.

SUMMARY OF THE INVENTION

One aspect of the invention relates to compounds of Formula I:

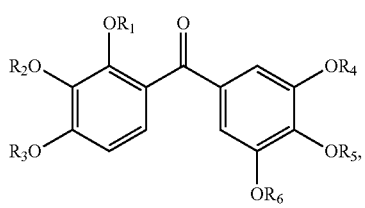

and pharmaceutically acceptable salts, hydrates, solvates, prodrugs, isomers, and tautomers thereof, wherein:

$R_1$, $R_2$, $R_3$, $R_4$, $R_5$ and $R_6$ are each independently H, $PO(OR_x)_2$, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), CO(heteroaryl), $CON(R_y)_2$, $COO(C_1$-$C_6$ alkyl), $COO(C_2$-$C_6$ alkenyl), $COO(C_2$-$C_6$ alkynyl), COO($C_3$-$C_8$ cycloalkyl), COO(3 to 8-membered heterocyclyl), or COO(aryl), COO(heteroaryl) wherein each $PO(OR_x)_2$, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), CO(heteroaryl), $CON(R_y)_2$, $COO(C_1$-$C_6$ alkyl), $COO(C_2$-$C_6$ alkenyl), $COO(C_2$-$C_6$ alkynyl), $COO(C_3$-$C_8$ cycloalkyl), COO(3 to 8-membered heterocyclyl), COO(aryl) or COO(heteroaryl) is optionally substituted with one or more substituents selected from the group consisting of halogen, OH, $NH_2$, CN, $C_1$-$C_6$ alkyl, aryl, heteroaryl and $C_1$-$C_6$ alkoxy;

$R_x$ is independently H, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) wherein each $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) is optionally substituted with one or more substituents selected from the group consisting of halogen, OH, $NH_2$, CN, $C_1$-$C_6$ alkyl, aryl, heteroaryl and $C_1$-$C_6$ alkoxy;

$R_y$ is independently H, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) wherein each $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) is optionally substituted with one or more substituents selected from the group consisting of halogen, OH, $NH_2$, CN, $C_1$-$C_6$ alkyl, aryl, heteroaryl and $C_1$-$C_6$ alkoxy;

provided that the compound is not:

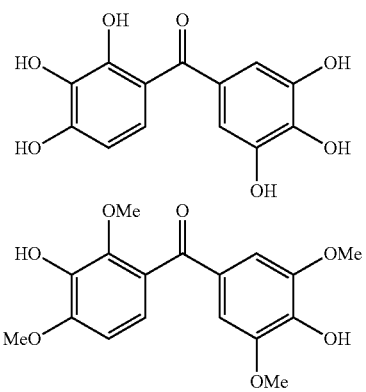

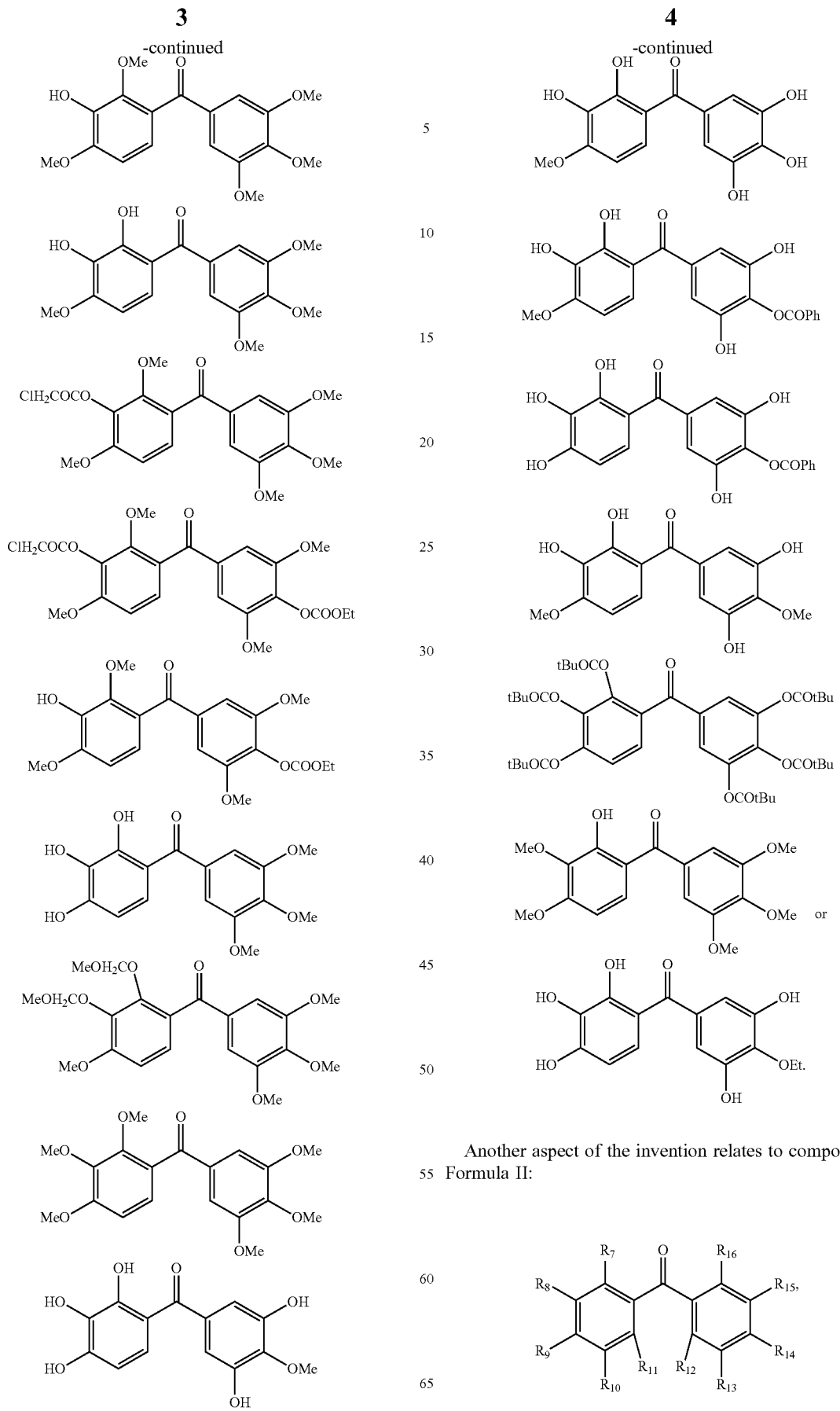
Another aspect of the invention relates to compounds of Formula II:

and pharmaceutically acceptable salts, hydrates, solvates, prodrugs, isomers, and tautomers thereof, wherein:

each $R_7$, $R_8$, $R_9$, $R_{10}$, $R_{11}$, $R_{12}$, $R_{13}$, $R_{14}$, $R_{15}$ and $R_{16}$ is independently H, OH or halogen provided that (1) at least two of $R_7$, $R_8$, $R_9$, $R_{10}$ and $R_{11}$ and at least two of $R_{12}$, $R_{13}$, $R_{14}$, $R_{15}$ and $R_{16}$ are both hydroxyl and adjacent to one another and that (2) the compound is not:

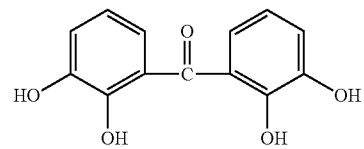
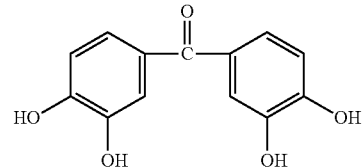
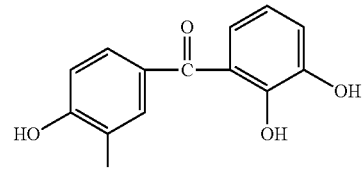
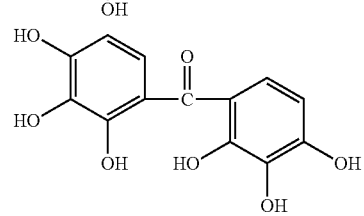
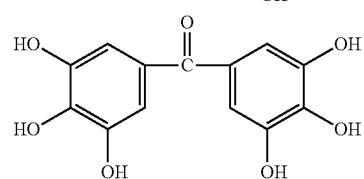
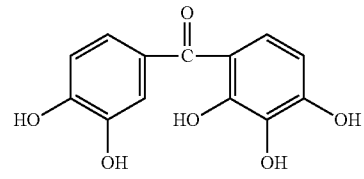
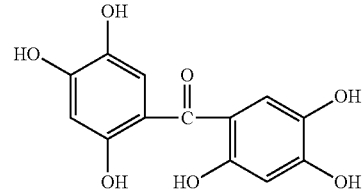
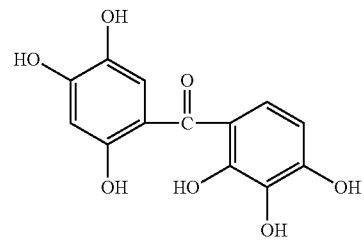

-continued

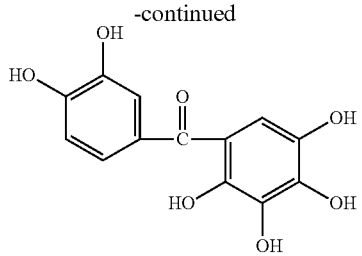
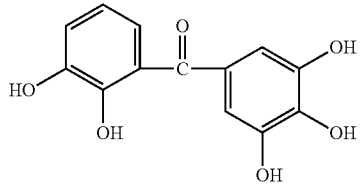
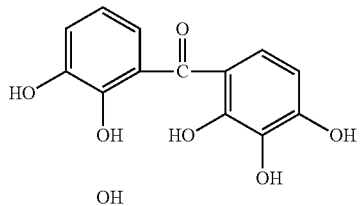
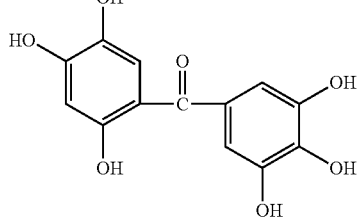
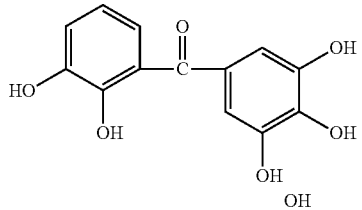
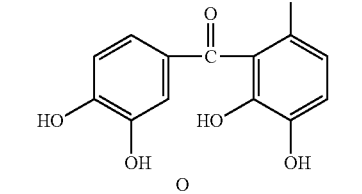
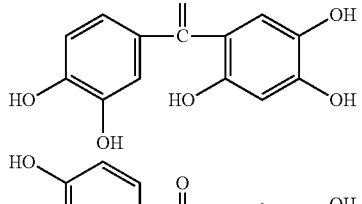
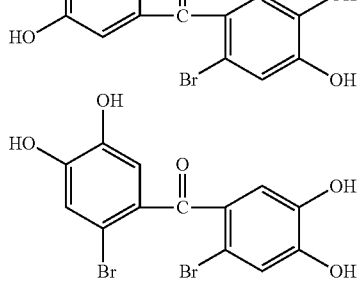

-continued
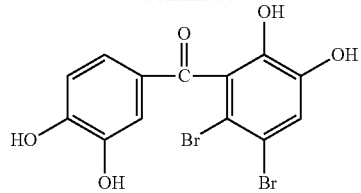
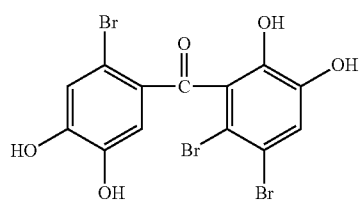
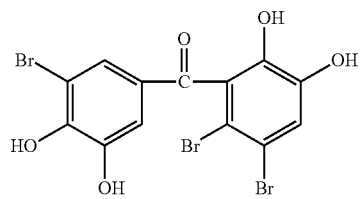
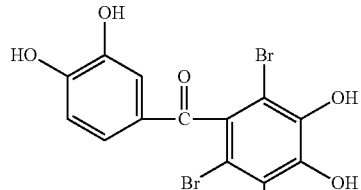
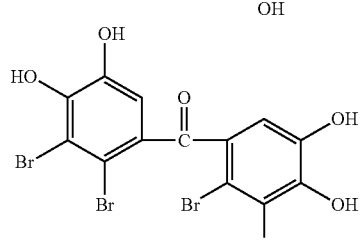
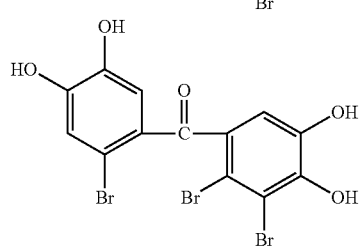
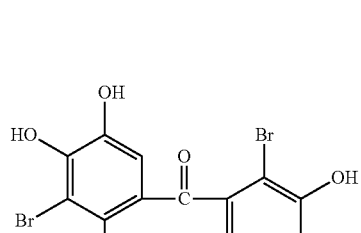
-continued
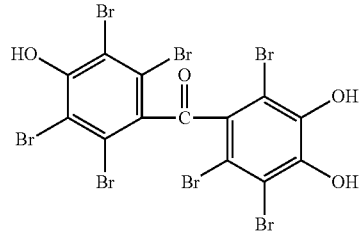
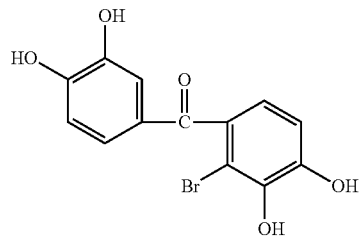
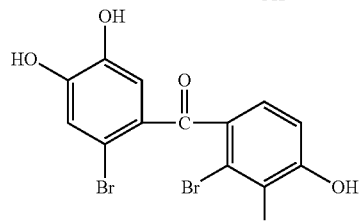
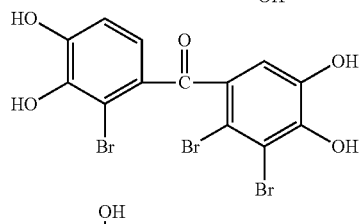
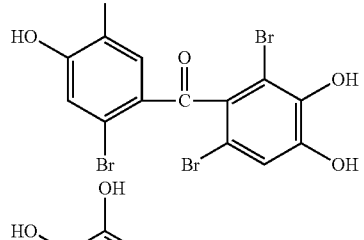
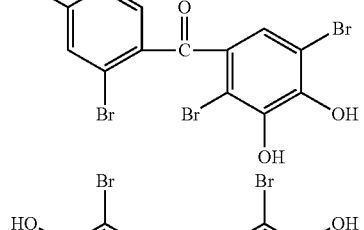
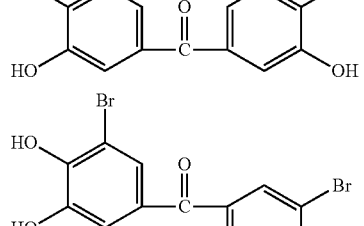

-continued

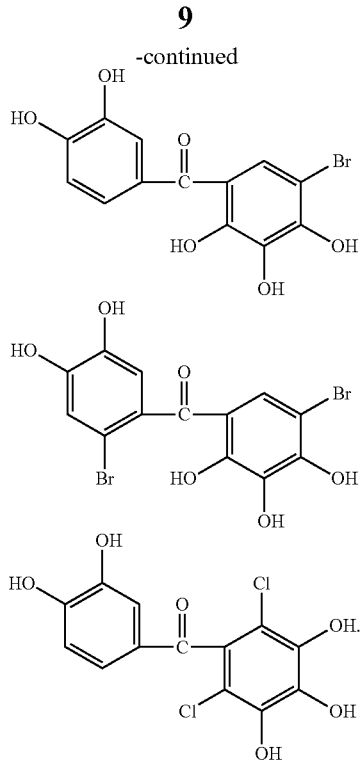

Another aspect of the invention relates to a method of treating a disease associated with a deficiency in HDAC1 deacetylase activity comprising administering to a patient in need thereof a compound of Formula I, Formula II or a pharmaceutically acceptable salt thereof.

Another aspect of the invention is directed to the use of a compound of Formula I or Formula II, or a pharmaceutically acceptable salt thereof, for activation of HDAC1.

Another aspect of the invention is directed to pharmaceutical compositions comprising a compound of Formula I or Formula II and a pharmaceutically acceptable carrier. The pharmaceutically acceptable carrier can further include an excipient, diluent, or surfactant. The pharmaceutical composition can be effective for treating a disease associated with a deficiency in HDAC1 deacetylase activity in a subject in need thereof. The pharmaceutical compositions can comprise the compounds of the present invention for use in treating diseases described herein.

Another aspect of the invention is directed to the use of a compound of Formula I or Formula II in the manufacture of a medicament for the treatment of a disease associated with a deficiency in HDAC1 deacetylase activity.

The present invention also provides methods for the treatment of human diseases or disorders including, without limitation, neurodegenerative, neurological disease, psychiatric disorders or cognitive deficits.

Additional features and advantages of the present technology will be apparent to one of skill in the art upon reading the Detailed Description of the Invention, below.

BRIEF DESCRIPTION OF THE DRAWINGS

FIGS. 3A-3C show that exifone is capable of reversing inhibition caused by preincubation of HDAC1 with active site HDAC inhibitor CI-994.

DETAILED DESCRIPTION OF THE INVENTION

Figure 1A:
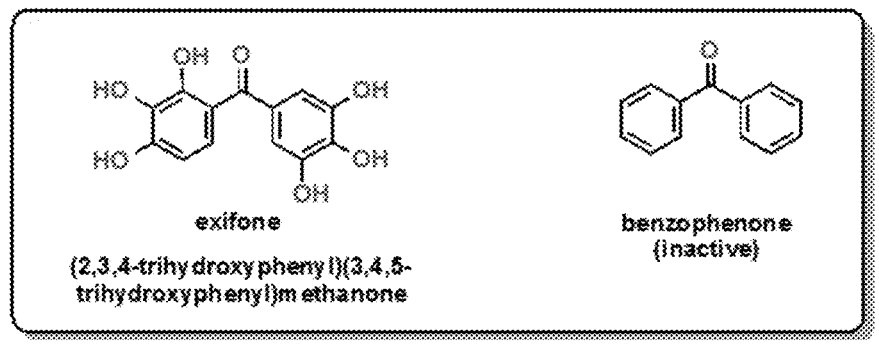
FIGS. 1A-1E show that exifone is a potent small molecule activator of HDAC1.

It has been unexpectedly observed that the polyhydroxylated benzophenone, exifone, increases the deacetylase activity of HDAC1, whereas the non-hydroxylated benzophenone does not. Described below are uses of exifone in the treatment of neurological disorders. Polyhydroxylated benzophenones of Formula I and Formula II are also described as is their use in treating neurological disorders.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$alkyl, —$C_1$-$C_6$alkyl, —O$C_2$-$C_6$alkenyl, —O$C_2$-$C_6$alkynyl, —$C_2$-$C_6$alkenyl, —$C_2$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, —NH$_2$, —NH($C_1$-$C_6$alkyl), —N($C_1$-$C_6$alkyl)$_2$, —S(O)$_2$—$C_1$-$C_6$alkyl, —S(O)NH$C_1$-$C_6$alkyl, and —S(O)N($C_1$-$C_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

The term "heteroaryl" means a monovalent monocyclic or bicyclic aromatic radical of 5 to 12 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom(s) is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof. Furthermore when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, and dihydrobenzoxanyl.

"Alkyl" refers to a straight or branched chain saturated hydrocarbon. $C_1$-$C_6$alkyl groups contain 1 to 6 carbon atoms. Examples of a $C_1$-$C_6$alkyl group include, but are not limited to, methyl, ethyl, propyl, butyl, pentyl, isopropyl, isobutyl, sec-butyl and tert-butyl, isopentyl and neopentyl.

"Alkylenyl" as herein defined refers to groups of general formula —(CH$_2$)n- where n is an integer from 1 to 6. Suitable examples of alkylenyl groups include methylenyl, ethylenyl, and propylenyl.

The term "alkenyl" means an aliphatic hydrocarbon group containing a carbon carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms.

The term "alkynyl" means an aliphatic hydrocarbon group containing a carbon carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 3-18 carbon atoms. Examples of cycloalkenyl groups include, without limitation, cyclopentenyl, cyclohexenyl, cycloheptenyl, cyclooctenyl, and norborenyl. A $C_3$-$C_8$ cycloalkenyl is a cycloalkenyl group containing between 3 and 8 carbon atoms.

The terms "heterocyclyl" or "heterocycloalkyl" or "heterocycle" refer to monocyclic or polycyclic 3 to 24-membered rings containing carbon and heteroatoms taken from oxygen, nitrogen, or sulfur and wherein there is not delocalized 7 electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heteroycyclyl or heterocycloalkyl ring can also be fused or bridged, e.g., can be a bicyclic ring.

As used herein, the term "halo" or "halogen" means fluoro, chloro, bromo, or iodo.

The term "carbonyl" refers to a functional group composing a carbon atom double-bonded to an oxygen atom. It can be abbreviated herein as "oxo", as C(O), or as C=O.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "stereoisomers" refers to the set of compounds which have the same number and type of atoms and share the same bond connectivity between those atoms, but differ in three dimensional structure. The term "stereoisomer" refers to any member of this set of compounds.

It should be understood that all isomeric forms are included within compounds of the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers. In some cases these diastereomers were separated and in other cases a wavy bond is used to indicate the structural element where configuration is variable.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the invention.

An "effective amount" when used in connection with a compound is an amount effective for treating or preventing a disease in a subject as described herein.

The term "composition" as used herein refers to a formulation of one or more compounds described herein that is capable of being administered or delivered to a patient and/or subject and/or cell. Typically, formulations include all physiologically acceptable compositions including derivatives and/or prodrugs, solvates, stereoisomers, racemates, or tautomers thereof with any physiologically acceptable carriers, diluents, and/or excipients. A "therapeutic composition" or "pharmaceutical composition" (used interchangeably herein) is a composition of one or more compounds capable of is capable of being administered or delivered to a patient and/or subject and/or cell for the treatment of a particular disease or disorder The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" or "treatment" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (i.e., using an enzyme).

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds disclosed herein may have one or more asymmetric carbon atom and may occur as racemates, racemic mixtures and as individual enantiomers or diastereomers.

A "patient" or "subject" is a mammal, e.g., a human, mouse, rat, guinea pig, dog, cat, horse, cow, pig, or non-human primate, such as a monkey, chimpanzee, baboon or rhesus.

Histone deacetylases (e.g. HDAC1) are enzymes that remove acetyl groups from proteins, including histones and result in increased chromatin compaction and decreased accessibility to DNA by proteins such as transcriptions factors. As used herein, "HDAC1 deacetylase activity" refers to the enzymatic activity HDAC1 and its ability to remove an acetyl group from a histone protein. A "deficiency in HDAC1 deacetylase activity" refers to a decrease or dysfunction in HDAC1 deacetylase activity. A deficiency in HDAC1 deacetylase activity may result from decreased expression of the HDAC1 gene, decreased HDAC1 protein expression, or decreased enzymatic activity of HDAC1 resulting from genetic mutations or exposure to an HDAC1 inhibitor.

"Activation of HDAC1" refers to activation of HDAC1 deacetylase activity (e.g., by treatment with exifone). In some embodiments, treatment with the compounds described herein results in an increase in HDAC1 by 1%, 10%, 20%, 30%, 40%, 50%, 100%, 200%, 300% or more.

"Neurodegenerative diseases" as used herein refers to any neurological disorder that may be reversed, improved, and/or eliminated by treatment (e.g., treatment with exifone).

In a first aspect of the invention, compounds of Formula I are provided:

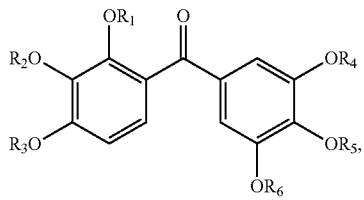

and pharmaceutically acceptable salts, hydrates, solvates, prodrugs, isomers, and tautomers thereof, wherein:
$R_1$, $R_2$, $R_3$, $R_4$, $R_5$, and $R_6$ are described as above;
provided that the compound is not:

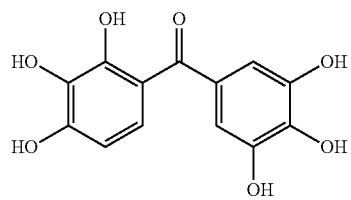

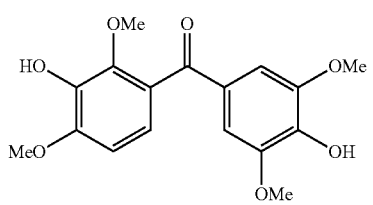

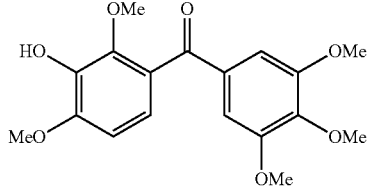

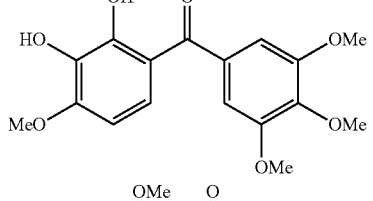

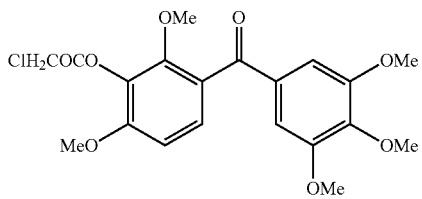

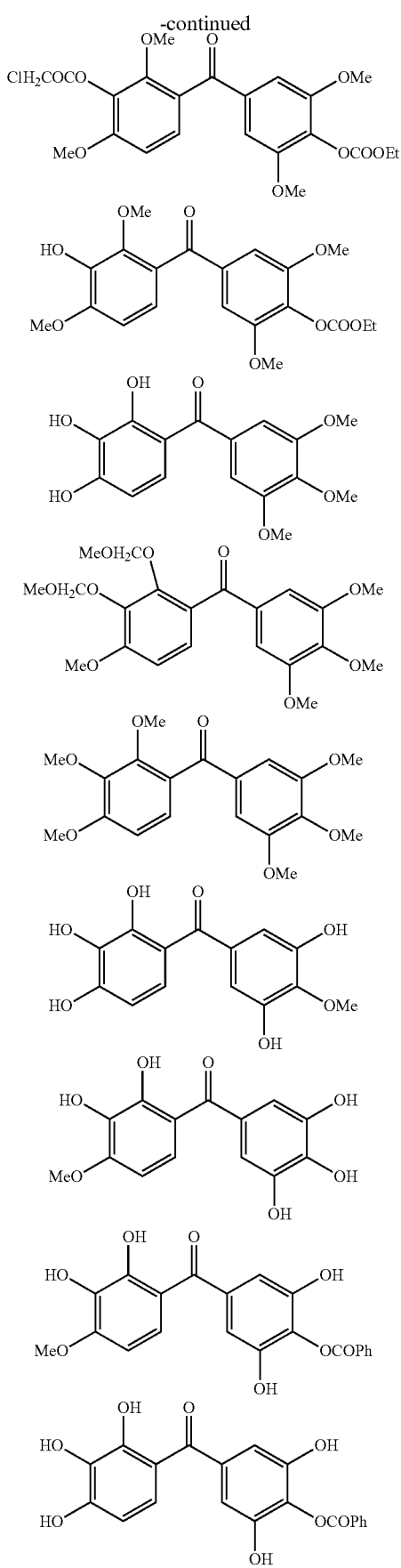

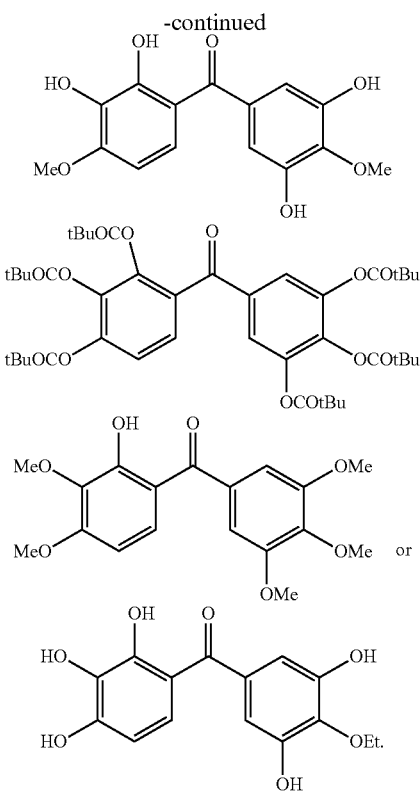

In some embodiments, the compounds of Formula I may be of the Formula Ia:

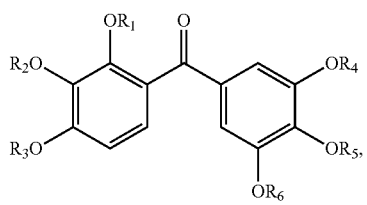

wherein:

$R_1$ is $PO(OR_x)_2$, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), $CO(3$ to 8-membered heterocyclyl), $CO(aryl)$, $CO(heteroaryl)$, $CON(R_y)_2$, $COO(C_1$-$C_6$ alkyl), $COO(C_2$-$C_6$ alkenyl), $COO(C_2$-$C_6$ alkynyl), $COO(C_3$-$C_8$ cycloalkyl), $COO(3$ to 8-membered heterocyclyl), $COO(aryl)$, or $COO(heteroaryl)$, wherein each $PO(OR_x)_2$, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), $CO(3$ to 8-membered heterocyclyl), $CO(aryl)$, $CO(heteroaryl)$, $CON(R_y)_2$, $COO(C_1$-$C_6$ alkyl), $COO(C_2$-$C_6$ alkenyl), $COO(C_2$-$C_6$ alkynyl), $COO(C_3$-$C_8$ cycloalkyl), $COO(3$ to 8-membered heterocyclyl), $COO(aryl)$ or $COO(heteroaryl)$ is optionally substituted with one or more substituents selected from the group consisting of halogen, OH, $NH_2$, CN, $C_1$-$C_6$ alkyl, aryl, heteroaryl and $C_1$-$C_6$ alkoxy;

$R_2$, $R_3$, $R_4$, $R_5$ and $R_6$ are each independently H, $PO(OR_x)_2$, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), $CO(3$ to 8-membered heterocyclyl), $CO(aryl)$, $CO(heteroaryl)$, $CON(R_y)_2$, $COO(C_1$-$C_6$ alkyl), $COO(C_2$-$C_6$ alkenyl), $COO(C_2$-$C_6$ alkynyl), $COO(C_3$-$C_8$ cycloalkyl), $COO(3$ to 8-membered heterocyclyl), $COO(aryl)$, $COO(heteroaryl)$ wherein each $PO(OR_x)_2$, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), $CO(3$ to 8-membered heterocyclyl), $CO(aryl)$, $CO(heteroaryl)$, $CON(R_y)_2$, $COO(C_1$-$C_6$ alkyl), $COO(C_2$-$C_6$ alkenyl), $COO(C_2$-$C_6$ alkynyl), $COO(C_3$-$C_8$ cycloalkyl), $COO(3$ to 8-membered heterocyclyl), $COO(aryl)$ or $COO(heteroaryl)$ is optionally substituted with one or more substituents selected from the group consisting of halogen, OH, $NH_2$, CN, $C_1$-$C_6$ alkyl, aryl, heteroaryl and $C_1$-$C_6$ alkoxy;

$R_x$ is H, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), $CO(3$ to 8-membered heterocyclyl), $CO(aryl)$, or $CO(heteroaryl)$ wherein each $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), $CO(3$ to 8-membered heterocyclyl), $CO(aryl)$, or $CO(heteroaryl)$ is optionally substituted with one or more substituents selected from the group consisting of halogen, OH, $NH_2$, CN, $C_1$-$C_6$ alkyl, aryl, heteroaryl and $C_1$-$C_6$ alkoxy; $R_y$ is H, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), $CO(3$ to 8-membered heterocyclyl), $CO(aryl)$, or $CO(heteroaryl)$ wherein each $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), $CO(3$ to 8-membered heterocyclyl), $CO(aryl)$, or $CO(heteroaryl)$ is optionally substituted with one or more substituents selected from the group consisting of halogen, OH, $NH_2$, CN, $C_1$-$C_6$ alkyl, aryl, heteroaryl and $C_1$-$C_6$ alkoxy;

provided that the compound is not:

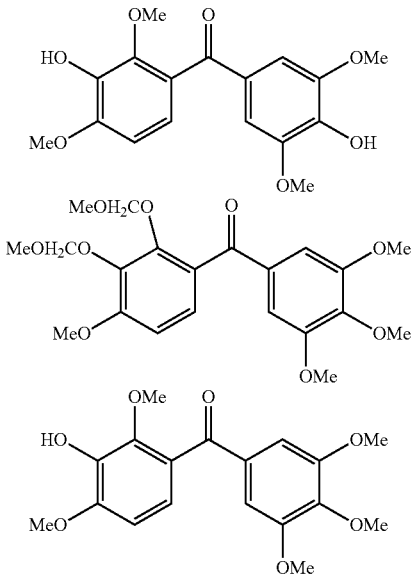

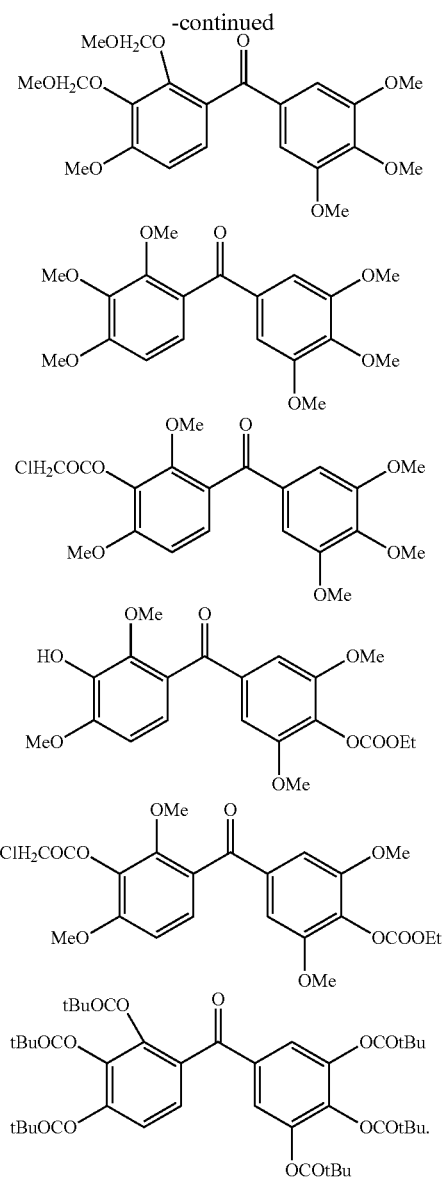

In other embodiments, the compounds of Formula I are of the Formula Ib:

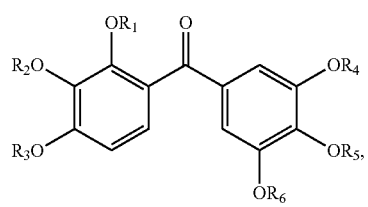

wherein:

$R_1$ is H, $PO(OR_x)_2$, $C_2$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), CO(heteroaryl), $CON(R_y)_2$, $COO(C_1$-$C_6$ alkyl), $COO(C_2$-$C_6$ alkenyl), $COO(C_2$-$C_6$ alkynyl), $COO(C_3$-$C_8$ cycloalkyl), COO(3 to 8-membered heterocyclyl), COO(aryl), or COO(heteroaryl) wherein each $PO(OR_x)_2$, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), CO(heteroaryl), $CON(R_y)_2$, $COO(C_1$-$C_6$ alkyl), $COO(C_2$-$C_6$ alkenyl), $COO(C_2$-$C_6$ alkynyl), $COO(C_3$-$C_8$ cycloalkyl), COO(3 to 8-membered heterocyclyl), COO(aryl) or COO(heteroaryl) is optionally substituted with one or more substituents selected from the group consisting of halogen, OH, $NH_2$, CN, $C_1$-$C_6$ alkyl, aryl, heteroaryl and $C_1$-$C_6$ alkoxy;

$R_2$, $R_3$, $R_4$, $R_5$ and $R_6$ are each independently H, $PO(OR_x)_2$, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), CO(heteroaryl), $CON(R_y)_2$, $COO(C_1$-$C_6$ alkyl), $COO(C_2$-$C_6$ alkenyl), $COO(C_2$-$C_6$ alkynyl), $COO(C_3$-$C_8$ cycloalkyl), COO(3 to 8-membered heterocyclyl), COO(aryl), or COO(heteroaryl) wherein each $PO(OR_x)_2$, $C_1$-$C_6$ alkyl, $C_2$-$C_6$ alkenyl, $C_2$-$C_6$ alkynyl, $C_3$—C cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), CO(heteroaryl), $CON(R_y)_2$, $COO(C_1$-$C_6$ alkyl), $COO(C_2$-$C_6$ alkenyl), $COO(C_2$-$C_6$ alkynyl), $COO(C_3$-$C_8$ cycloalkyl), COO(3 to 8-membered heterocyclyl), COO(aryl) or COO(heteroaryl) is optionally substituted with one or more substituents selected from the group consisting of halogen, OH, $NH_2$, CN, $C_1$-$C_6$ alkyl, aryl, heteroaryl and $C_1$-$C_6$ alkoxy;

$R_x$ is independently H, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) wherein each $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) is optionally substituted with one or more substituents selected from the group consisting of halogen, OH, $NH_2$, CN, $C_1$-$C_6$ alkyl, aryl, heteroaryl and $C_1$-$C_6$ alkoxy;

$R_y$ is independently H, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) wherein each $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) is optionally substituted with one or more substituents selected from the group consisting of halogen, OH, $NH_2$, CN, $C_1$-$C_6$ alkyl, aryl, heteroaryl and $C_1$-$C_6$ alkoxy;

provided that the compound is not:

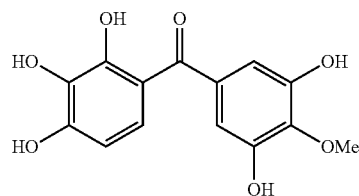

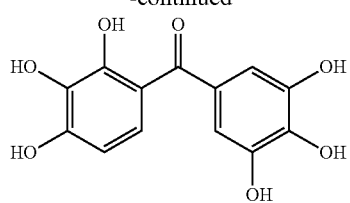
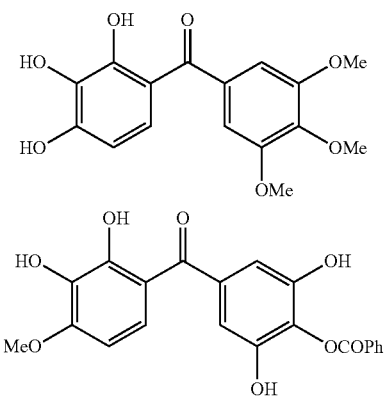
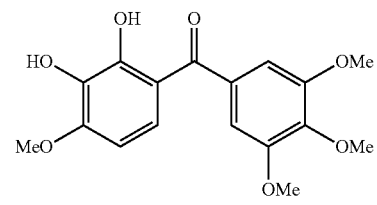
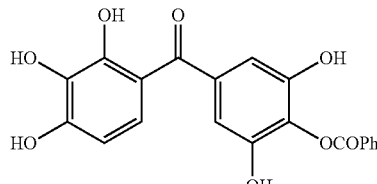
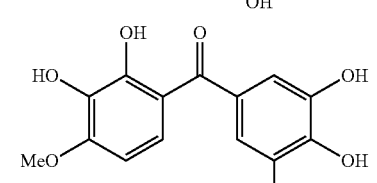
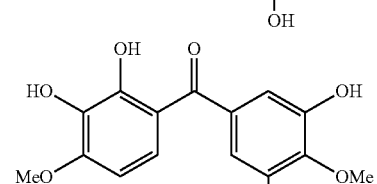
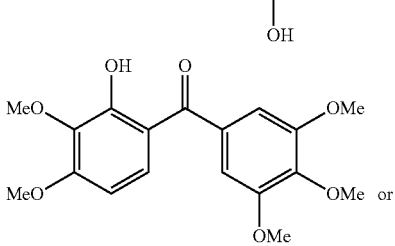

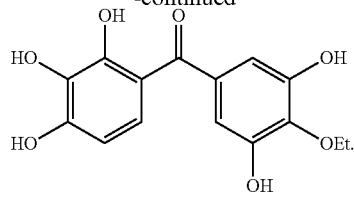
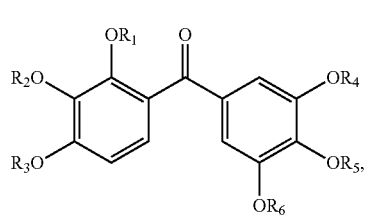

In other embodiments of the invention, the compounds of Formula I are of the Formula Ic:

$$\text{Ic}$$

wherein:

$R_1$, $R_2$, $R_3$, $R_4$, $R_5$ and $R_6$ are each independently $PO(OR_x)_2$, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), CO(heteroaryl), $CON(R_y)_2$, $COO(C_1$-$C_6$ alkyl), $COO(C_2$-$C_6$ alkenyl), $COO(C_2$-$C_6$ alkynyl), $COO(C_3$-$C_8$ cycloalkyl), COO(3 to 8-membered heterocyclyl), or COO(aryl), COO(heteroaryl) wherein each $PO(OR_x)_2$, $CO(C_1$-$C_6$ alkyl), $CO(C_2$-$C_6$ alkenyl), $CO(C_2$-$C_6$ alkynyl), $CO(C_3$—C cycloalkyl), CO(3 to 8-membered heterocyclyl), CO(aryl), CO(heteroaryl), $CON(R_y)_2$, $COO(C_1$-$C_6$ alkyl), $COO(C_2$-$C_6$ alkenyl), $COO(C_2$-$C_6$ alkynyl), $COO(C_3$-$C_8$ cycloalkyl), COO(3 to 8-membered heterocyclyl), COO(aryl) or COO(heteroaryl) is optionally substituted with one or more substituents selected from the group consisting of halogen, OH, $NH_2$, CN, $C_1$-$C_6$ alkyl, aryl, heteroaryl and $C_1$-$C_6$ alkoxy;

$R_x$ is independently H, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) wherein each $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) is optionally substituted with one or more substituents selected from the group consisting of halogen, OH, $NH_2$, CN, $C_1$-$C_6$ alkyl, aryl, heteroaryl and $C_1$-$C_6$ alkoxy;

$R_y$ is independently H, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) wherein each $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) is optionally substituted with one or more substituents selected from the group consisting of halogen, OH, $NH_2$, CN, $C_1$-$C_6$ alkyl, aryl, heteroaryl and $C_1$-$C_6$ alkoxy;

provided that the compound is not:

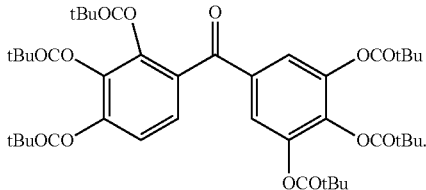

In other embodiments, the compounds of Formula I are of the Formula Id:

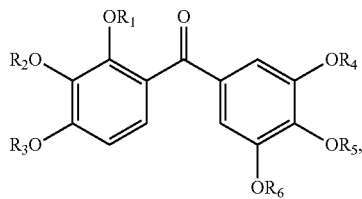

wherein:

$R_1$, $R_2$, $R_3$, $R_4$, $R_5$ and $R_6$ each are independently $PO(OR_x)_2$, $CO(C_1-C_6$ alkyl), $CO$(aryl), $CO$(heteroaryl), $CON(R_y)_2$, $COO(C_1-C_6$ alkyl), $COO$(aryl), $COO$(heteroaryl), wherein each $PO(OR_x)_2$, $CO(C_1-C_6$ alkyl), $CO$(aryl), $CO$(heteroaryl), $CON(R_y)_2$, $COO(C_1-C_6$ alkyl), $COO$(aryl), $COO$(heteroaryl) is optionally substituted with one or more substituents selected from the group consisting of halogen, OH, $NH_2$, CN, $C_1-C_6$ alkyl, aryl, heteroaryl and $C_1-C_6$ alkoxy;

$R_x$ is independently H, $C_1-C_6$ alkyl, $C_2-C_6$ alkenyl, $C_2-C_6$ alkynyl, $C_3-C_8$ cycloalkyl, 3 to 8-membered heterocyclyl, aryl, heteroaryl, $CO(C_1-C_6$ alkyl), $CO(C_2-C_6$ alkenyl), $CO(C_2-C_6$ alkynyl), $CO(C_3-C_8$ cycloalkyl), CO(3 to 8-membered heterocyclyl), CO(aryl), or CO(heteroaryl) wherein each $C_1-C_6$ alkyl, $C_2-C_6$ alkenyl, $C_2-C_6$ alkynyl, $C_3-C_8$ cycloalkyl, 3 to 8-membered heterocyclyl, aryl, heteroaryl, $CO(C_1-C_6$ alkyl), $CO(C_2-C_6$ alkenyl), $CO(C_2-C_6$ alkynyl), $CO(C_3-C_8$ cycloalkyl), CO(3 to 8-membered heterocyclyl), CO(aryl), or CO(heteroaryl) is optionally substituted with one or more substituents selected from the group consisting of halogen, OH, $NH_2$, CN, $C_1-C_6$ alkyl, aryl, heteroaryl and $C_1-C_6$ alkoxy;

$R_y$ is independently H, $C_1-C_6$ alkyl, $C_2-C_6$ alkenyl, $C_2-C_6$ alkynyl, $C_3-C_8$ cycloalkyl, 3 to 8-membered heterocyclyl, aryl, heteroaryl, $CO(C_1-C_6$ alkyl), $CO(C_2-C_6$ alkenyl), $CO(C_2-C_6$ alkynyl), $CO(C_3-C_8$ cycloalkyl), CO(3 to 8-membered heterocyclyl), CO(aryl), or CO(heteroaryl) wherein each $C_1-C_6$ alkyl, $C_2-C_6$ alkenyl, $C_2-C_6$ alkynyl, $C_3-C_8$ cycloalkyl, 3 to 8-membered heterocyclyl, aryl, heteroaryl, $CO(C_1-C_6$ alkyl), $CO(C_2-C_6$ alkenyl), $CO(C_2-C_6$ alkynyl), $CO(C_3-C_8$ cycloalkyl), CO(3 to 8-membered heterocyclyl), CO(aryl), or CO(heteroaryl) is optionally substituted with one or more substituents selected from the group consisting of halogen, OH, $NH_2$, CN, $C_1-C_6$ alkyl, aryl, heteroaryl and $C_1-C_6$ alkoxy;

provided that the compound is not:

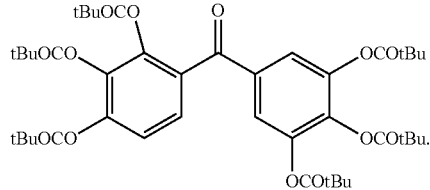

In other embodiments, the compounds of Formula Id may be of the Formula Id-1:

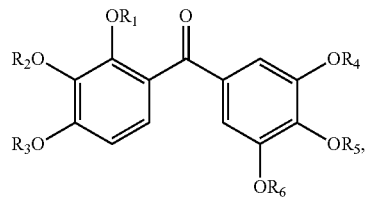

wherein:

$R_1$, $R_2$, $R_3$, $R_4$, $R_5$ and $R_6$ are each independently [PO$(OR_x)_2$, $CON(R_y)_2$, $COO(C_1-C_6$ alkyl), $COO$(aryl), $COO$(heteroaryl) are removed and $CO(C_3-C_6$ cycloalkyl) and $CO(C_3-C_6$ heterocyclyl) were added] $CO(C_1-C_6$ alkyl), $CO(C_3-C_6$ cycloalkyl), $CO(C_3-C_6$ heterocyclyl), $CO$(aryl), $CO$(heteroaryl), wherein each $CO(C_1-C_6$ alkyl), $CO(C_3-C_6$ cycloalkyl), $CO(C_3-C_6$ heterocycle), $CO$(aryl) or $CO$(heteroaryl) is optionally substituted with one or more substituents selected from the group consisting of halogen, OH, $NH_2$, CN, $C_1-C_6$ alkyl, aryl, heteroaryl and $C_1-C_6$ alkoxy;

provided that the compound is not:

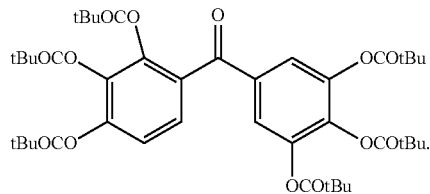

In other embodiments, the compounds of Formula I may be of the Formula Ie:

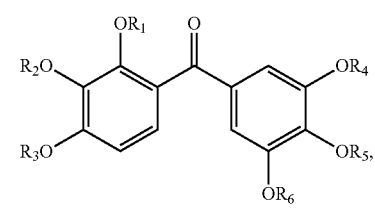

wherein:

$R_1$, $R_2$, $R_3$, $R_4$, $R_5$ and $R_6$ are each independently $CO(C_1-C_3$ alkyl), wherein $CO(C_1-C_3$ alkyl) is optionally substituted with one or more substituents selected from the group consisting of halogen, OH, $NH_2$, CN, $C_1-C_6$ alkyl, aryl, heteroaryl and $C_1-C_6$ alkoxy.

In another embodiment of the compounds of Formula Ie, each of $R_1$, $R_2$, $R_3$, $R_4$, $R_5$ and $R_6$ is $CO(C_1-C_2$ alkyl).

In another embodiment of the compounds of Formula Ie, each of $R_1$, $R_2$, $R_3$, $R_4$, $R_5$ and $R_6$ is $CO(C_1$ alkyl).

In an illustrative embodiment the compound of Formula I is I-1:

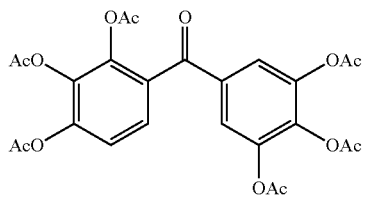

I-1

In another illustrative embodiment the compound of Formula I is:

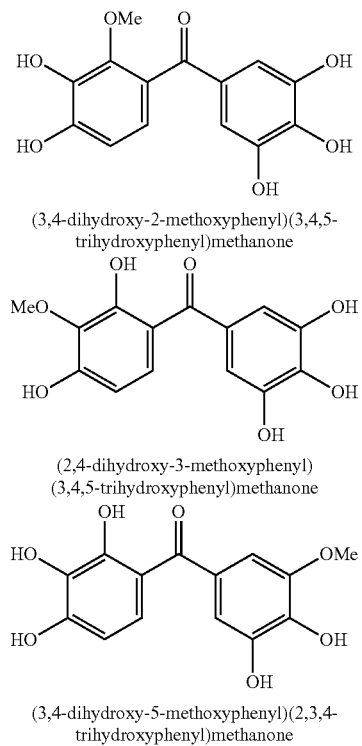

(3,4-dihydroxy-2-methoxyphenyl)(3,4,5-trihydroxyphenyl)methanone (2,4-dihydroxy-3-methoxyphenyl)(3,4,5-trihydroxyphenyl)methanone (3,4-dihydroxy-5-methoxyphenyl)(2,3,4-trihydroxyphenyl)methanone In another aspect of the invention, pharmaceutical compositions comprising compounds of Formulae I, Ia, Ib, Ic, Id, Id-1, Ie, II, IIa, IIb, or IIc, and pharmaceutically acceptable carriers are provided.

In another aspect of the invention, methods of treating a disease associated with a deficiency in HDAC1 deacetylase activity are provided, the methods comprising administering to a patient in need thereof compounds of Formula I or a pharmaceutically acceptable salt thereof.

In another aspect of the invention, methods of treating neurodegenerative disease, neurological disorder, psychiatric disorder, or cognitive deficit comprising administering to a patient in need thereof compounds of Formula I or a pharmaceutically acceptable salt thereof.

In another aspect of the invention, methods of treating dementia (e.g. Alzheimer's disease or frontotemporal dementia) are provided, the methods comprising administering to a patient in need thereof compounds of Formula I or a pharmaceutically acceptable salt thereof.

In another aspect of the invention, methods of treating neurodegenerative disorders (e.g. amytrophic lateral sclerosis (ALS) and other motor neuron degenerative disorders) are provided, the methods comprising administering to a patient in need thereof compounds of Formula I or a pharmaceutically acceptable salt thereof.

In another aspect of the invention, methods of treating psychiatric disorders (e.g. major depression, bipolar disorder, and schizophrenia) are provided, the methods comprising administering to a patient in need thereof compounds of Formula I or a pharmaceutically acceptable salt thereof.

In some embodiments of the invention, administration to a patient is performed orally, parenterally, intranasally, subcutaneously, by injection or by infusion.

In other embodiments of the invention are compounds of Formulae I, Ia, Ib, Ic, Id, Id-1, Ie, II, IIa, IIb, or IIc, for use in the manufacture of a medicament for treating a disease or disorder associated with a deficiency in HDAC1 deacetylase activity.

In other embodiments of the invention are uses of compounds of Formulae I, Ia, Ib, Ic, Id, Id-1, Ie, II, IIa, IIb, or IIc, for treating a disease or disorder associated with a deficiency in HDAC1 deacetylase activity.

In other embodiments of the invention are uses of compounds of Formulae I, Ia, Ib, Ic, Id, Id-1, Ie, II, IIa, IIb, or IIc, for activation of HDAC1.

In other embodiments of the invention are methods of activating HDAC1 activity comprising contacting a cell with compounds of Formulae I, Ia, Ib, Ic, Id, Id-1, Ie, II, IIa, IIb, or IIc.

In a second aspect of the invention, compounds of the Formula II are provided:

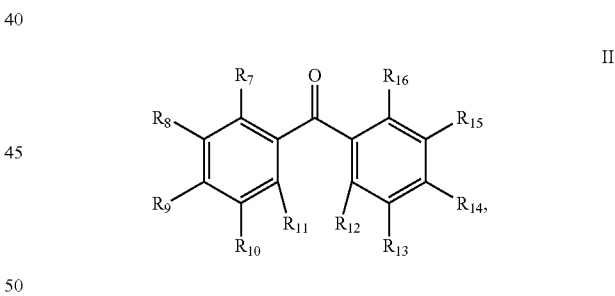

II and pharmaceutically acceptable salts, hydrates, solvates, prodrugs, isomers, and tautomers thereof, wherein:

each $R_7$, $R_8$, $R_9$, $R_{10}$, $R_{11}$, $R_{12}$, $R_{13}$, $R_{14}$, $R_{15}$ and $R_{16}$ is independently H, OH or halogen provided that (1) at least two of $R_7$, $R_8$, $R_9$, $R_{10}$ and $R_{11}$ and at least two of $R_{12}$, $R_{13}$, $R_{14}$, $R_{15}$ and $R_{16}$ are both hydroxyl and adjacent to one another and that (2) the compound is not: provided that the compound is not:

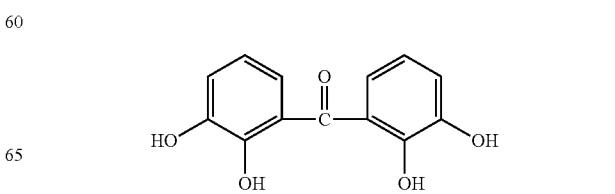

-continued
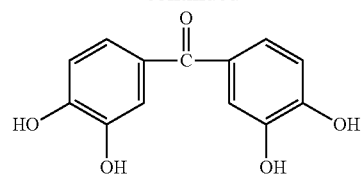
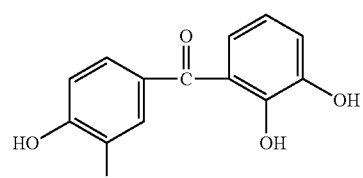
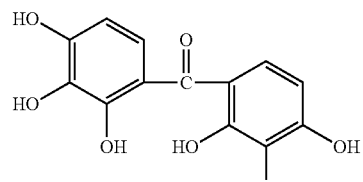
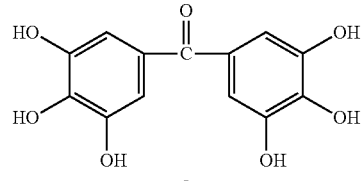
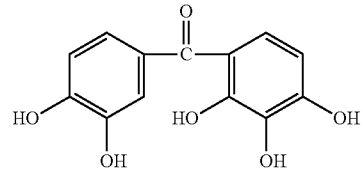
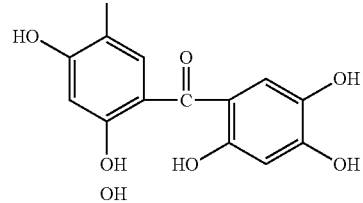
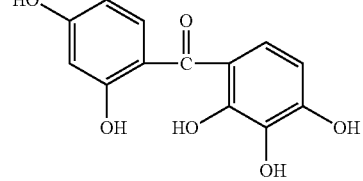
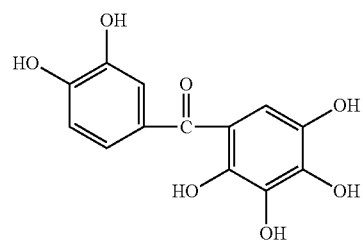
-continued
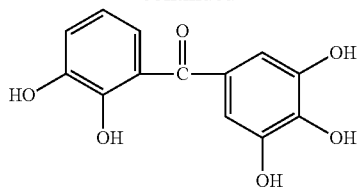
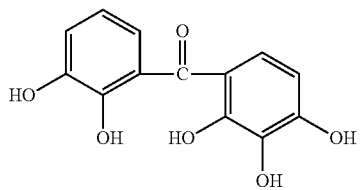
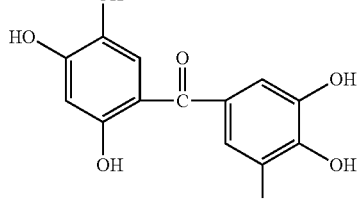
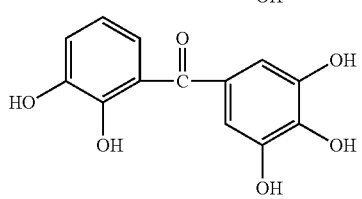
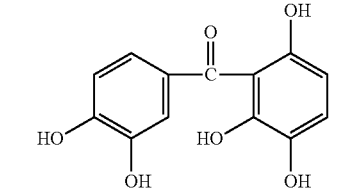
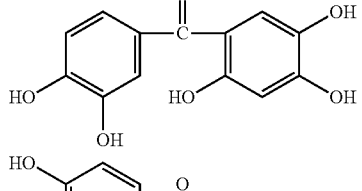
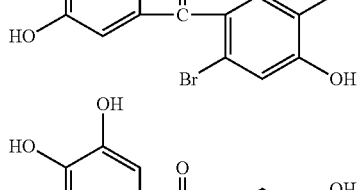
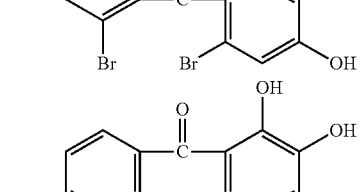

-continued
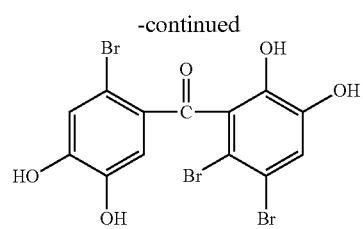
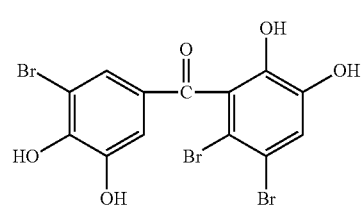
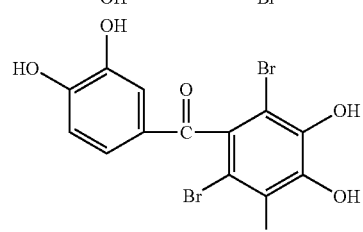
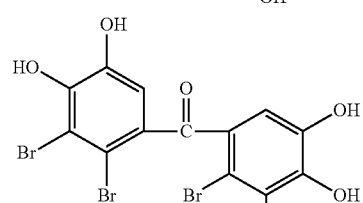
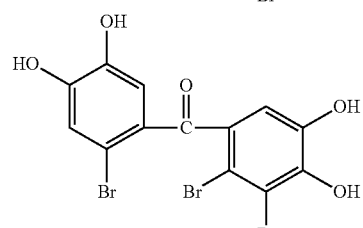
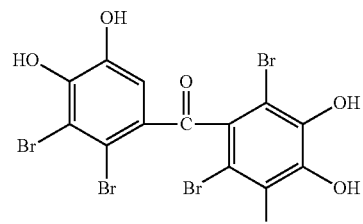
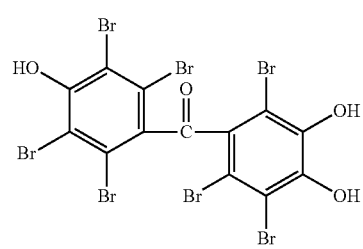
-continued
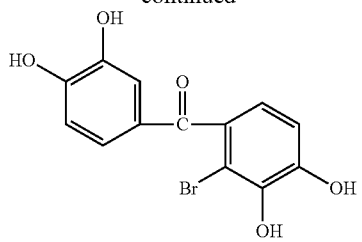
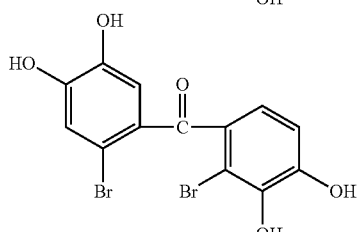
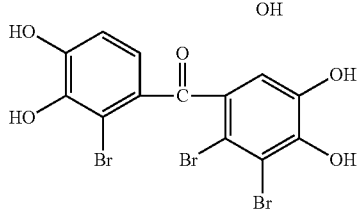
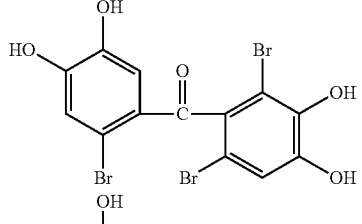
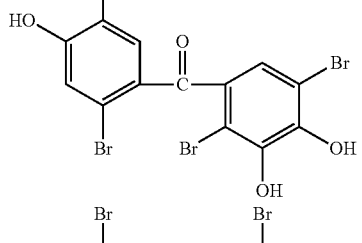
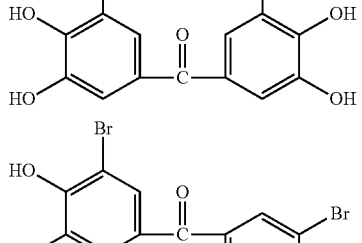
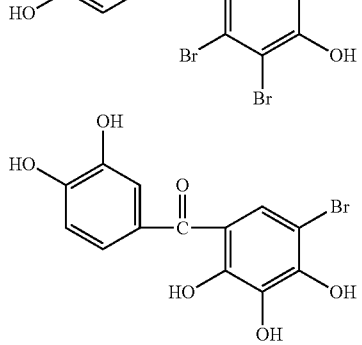

-continued

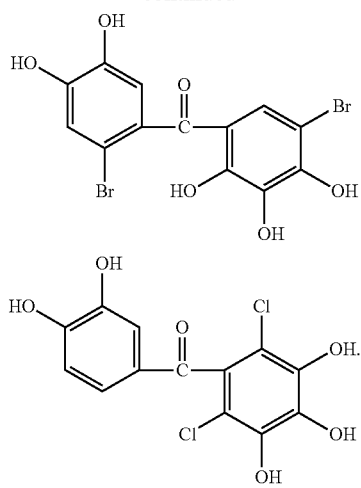

In some embodiments of the invention, the compounds of Formula II are of the Formula IIa:

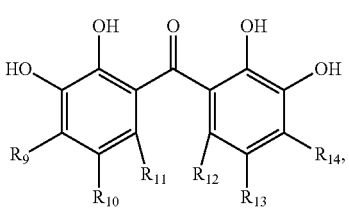

wherein $R_9$, $R_{10}$, $R_{11}$, $R_{12}$, $R_{13}$ and $R_{14}$, are each independently H, OH or halogen, and provided that the compound is not:

In other embodiments, the compounds of Formula II are of the Formula IIb:

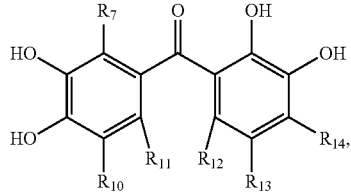

wherein $R_7$, $R_{10}$, $R_{11}$, $R_{12}$, $R_{13}$ and $R_{14}$ are each independently H, OH or halogen, and provided that the compound is not:

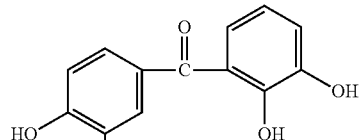

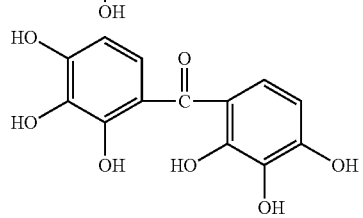

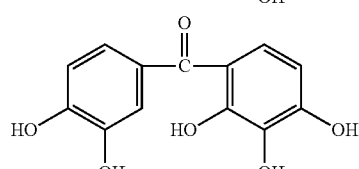

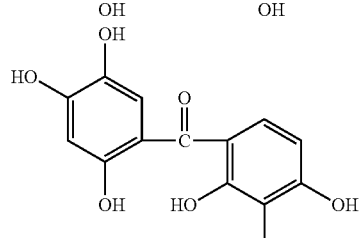

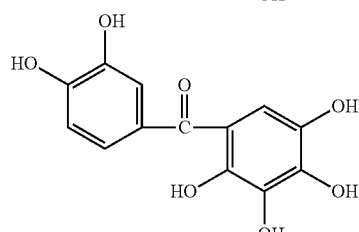

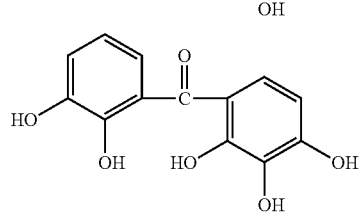

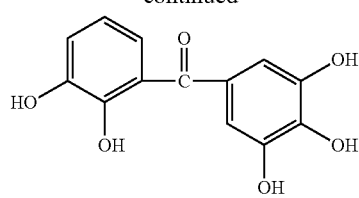
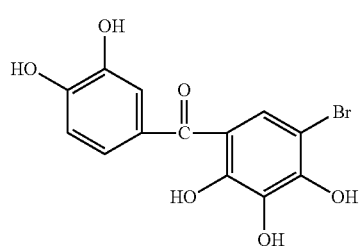
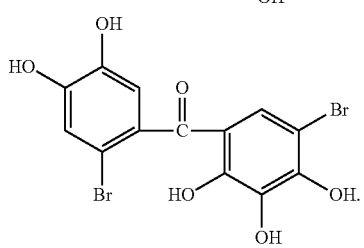
In other embodiments, the compounds of Formula II are of the Formula IIc:
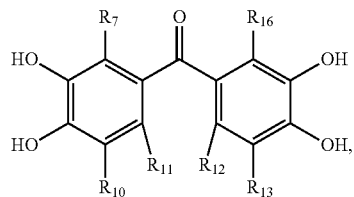
wherein $R_7$, $R_{10}$, $R_{11}$, $R_{12}$, $R_{13}$ and $R_{16}$ are each independently H, OH or halogen, and provided that the compound is not:
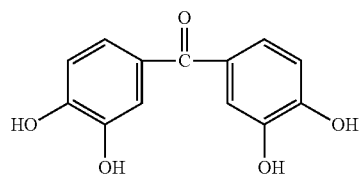
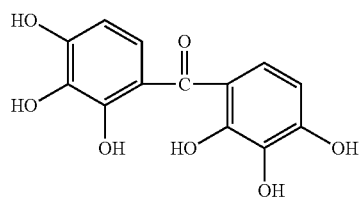
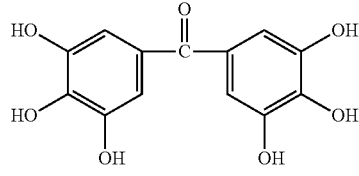
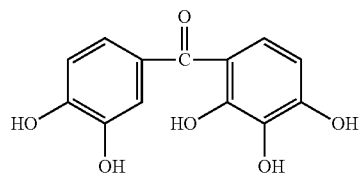
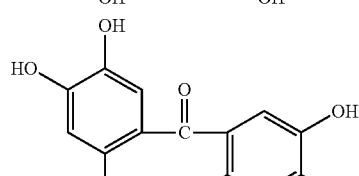
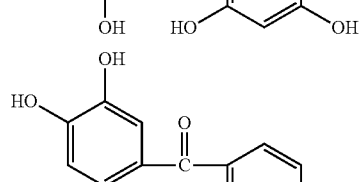
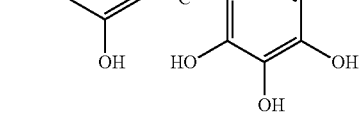

-continued
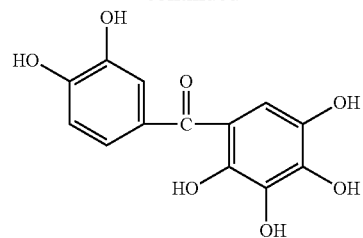
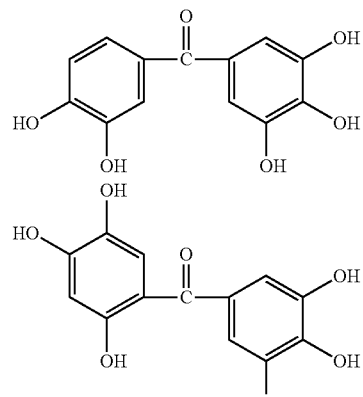
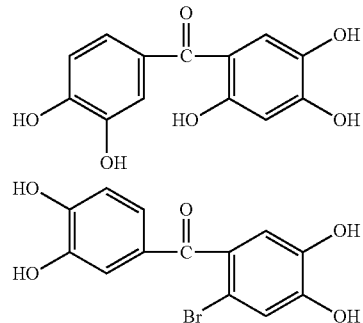
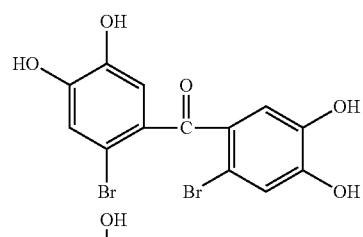
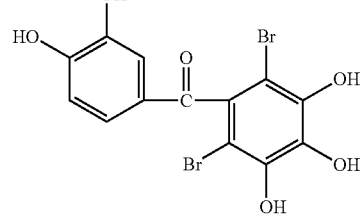
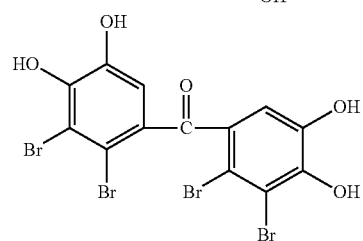
-continued
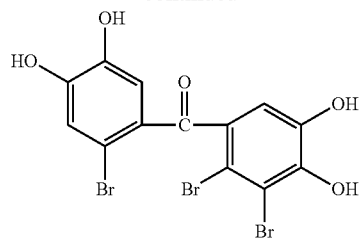
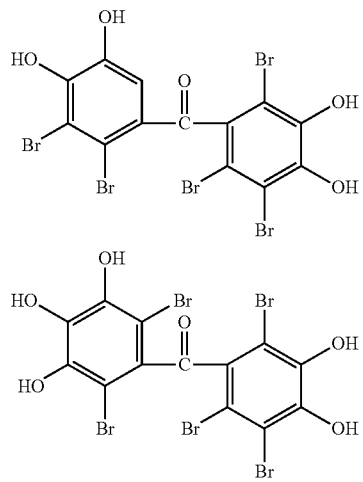
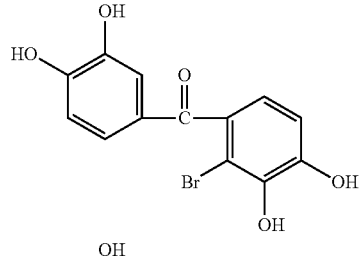
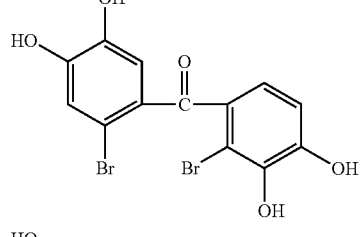
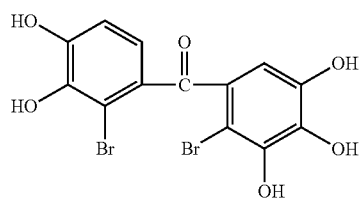
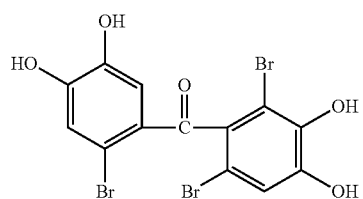

-continued

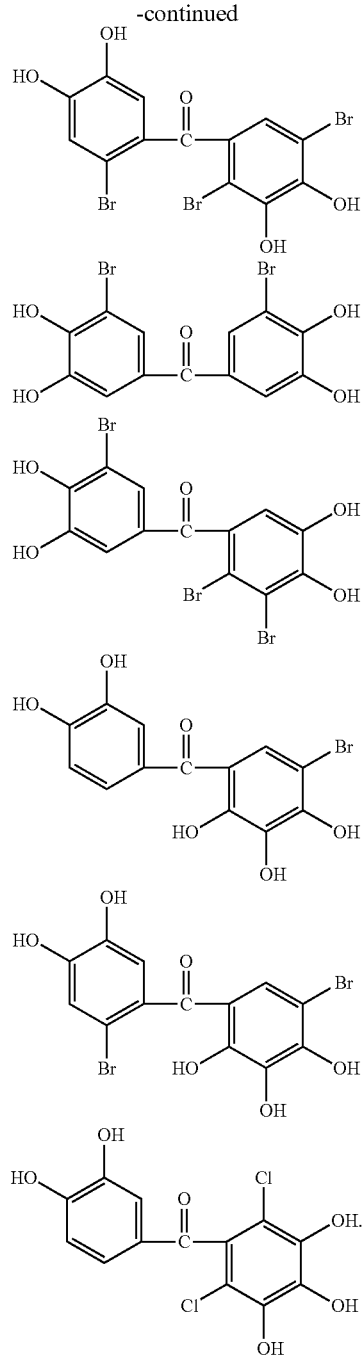

In an illustrative embodiment, the compound of Formula II is II-1:

II-1

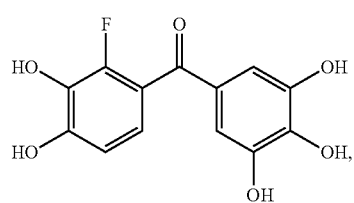

In another illustrative embodiment the compound of Formula II is:

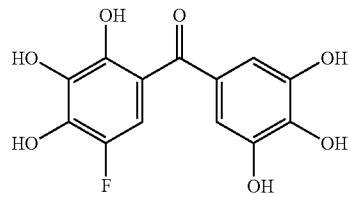

(5-fluoro-2,3,4-trihydroxyphenyl)
(3,4,5-trihydroxyphenyl)methanone

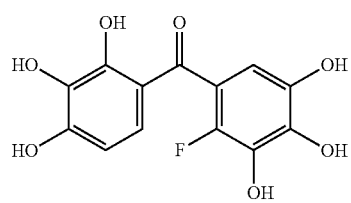

(2-fluoro-3,4,5-trihydroxyphenyl)
(2,3,4-trihydroxyphenyl)methanone

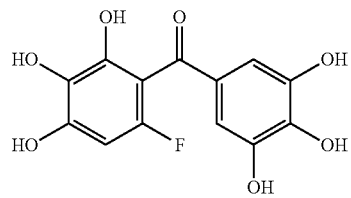

(6-fluoro-2,3,4-trihydroxyphenyl)
(3,4,5-trihydroxyphenyl)methanone

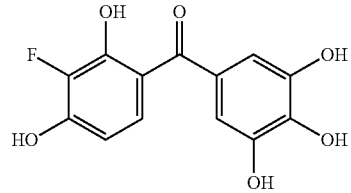

(3-fluoro-2,4-dihydroxyphenyl)
(3,4,5-trihydroxyphenyl)methanone

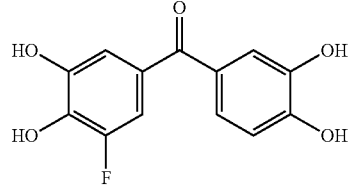

(3,4-dihydroxyphenyl)
(3-fluoro-4,5-dihydroxyphenyl)methanone

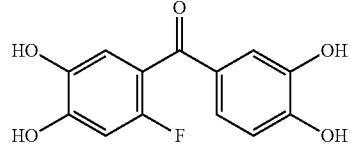

(3,4-dihydroxyphenyl)
(2-fluoro-4,5-dihydroxyphenyl)methanone

-continued

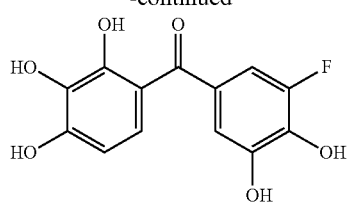

(3-fluoro-4,5-dihydroxyphenyl)
(2,3,4-trihydroxyphenyl)methanone

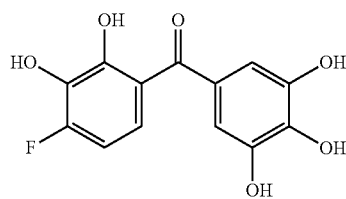

(4-fluoro-2,3-dihydroxyphenyl)
(3,4,5-trihydroxyphenyl)methanone

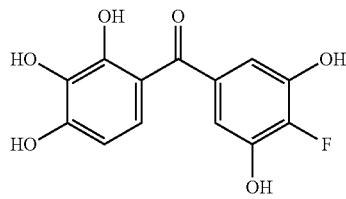

(4-fluoro-3,5-dihydroxyphenyl)
(2,3,4-trihydroxyphenyl)methanone

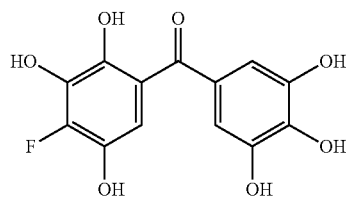

(4-fluoro-2,3,5-trihydroxyphenyl)
(3,4,5-trihydroxyphenyl)methanone

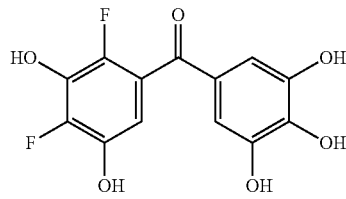

(2-fluoro-3,4,5-trihydroxyphenyl)
(3,4,5-trihydroxyphenyl)methanone

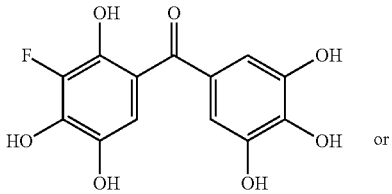

(3-fluoro-2,4,5-trihydroxyphenyl)
(3,4,5-trihydroxyphenyl)methanone or

-continued

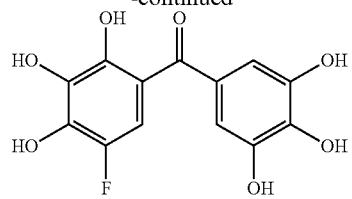

(5-fluoro-2,3,4-trihydroxyphenyl)
(3,4,5-trihydroxyphenyl)methanone

In further embodiments, kits are provided which comprise compounds of Formula I or Formula II or a pharmaceutically acceptable salt and a compound effective in treating a disease responsive to HDAC1 activation as defined above. In some embodiments the compounds effective in treating a disease responsive to HDAC1 activity is selected from the group consisting of Aricept®, Exelon®, Razadyne®, Cognex® and Namenda®.

In further embodiments are uses of compounds of Formula I or Formula II or a pharmaceutically acceptable salt in combination with tests to monitor liver function through assessment of serum aminotransferase activity and other markers to improve safety.

In further embodiments of the invention are uses of compounds of Formula I or Formula II or a pharmaceutically acceptable salt in combination with genetic tests to monitor liver metabolic enzyme genotypes to improve safety.

It should be understood that all isomeric forms are included within compounds of the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Methods of Synthesizing the Disclosed Compounds

The compounds of the present invention may be made by a variety of methods, including standard chemistry. Suitable synthetic routes are depicted in the schemes given below.

The compounds of Formula I and Formula II may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I or Formula II.

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below.

General Synthesis of Polyhydroxylated Benzophenones Described in the Invention.

Compounds of the present invention may generally be prepared as described in U.S. Pat. No. 4,015,017. Specifically, these compounds may be prepared by reacting a polyhydroxylated aromatic carboxylic acid with a polyhydroxylated aromatic compound in the presence of anhydrous zinc chloride and phosphorous oxychloride, according to a reaction of the Fries type (Fries and Finck, Chen Ber., 41:4271, 1908).

Methods of Using the Disclosed Compounds

The compounds of Formula I and Formula II can be used to treat neurological diseases, including neurodegenerative diseases, psychiatric disorders, and cognitive disorders. Neurological disorders are understood as disorders of the central or peripheral nervous system (e.g., the brain, spinal cord, and connecting nerves). Neurological disorders can include, but are not limited to, epilepsy, attention deficit disorder (ADD), Alzheimer's disease (AD), Parkinson's Disease, Huntington's Disease, essential tremor, central nervous system trauma caused by tissue injury, oxidative stress-induced neuronal or axomal degeneration, multiple sclerosis, dementia, frontotemporal dementia, austim spectrum disorder, dyslexia, dyspraxia, amyotrophic lateral sclerosis (ALS), aphasia, apraxia, ataxia, palsies, motor neuron diseases, muscular dystrophy, traumatic brain injury, or ischemic brain injury.

Psychiatric disorders refer to behavior or mental patterns affecting how a patient behaves, perceives, or thinks. Psychiatric disorders can include, but are not limited to, bipolar disorder, schizophrenia, and major depression, anxiety disorders, eating disorders, addiction and control disorders, obsessive-compulsive disorder, and post-traumatic stress disorder.

In some embodiments, the compounds disclosed herein are used to treat disorders associated with a deficiency HDAC1 deacetylase activity including but not limited to, AD, Parkinson's Disease, Huntington's Disease, frontotemporal dementia, or ALS. In some embodiments, the administration of the compounds described herein increases HDAC1 deacetylase activity. The effects of a particular compound on HDAC1 activity can be determined by methods known in the art including Western Blot analysis for deacetylation of histones or high throughput mass spectrometry assays such as the RapidFire™ platform, among others.

In some embodiments, the compounds described herein result upregulate genes associated with particular immune pathways or neurogenesis pathways. In particular embodiments, the compounds result in the upregulation of genes associated with cytokine signaling, such as interferon (IFN) signaling, including IFNα, IFNβ, and/or IFNγ. Upregulation of genes associated with particular pathways can be determined by methods known in the art including qPCR and next-generation sequencing (RNA-Seq) among others. In some embodiments, determining the upregulation of genes associated with particular pathways requires the collection of a sample from the subject or patient. The term "sample" refers to a volume and/or mass obtained, provided, and/or subjected to analysis. In some embodiments, a sample comprises a tissue sample, cell sample, a fluid sample, and the like. In some embodiments, a sample is taken from a subject (e.g., a human or animal subject). In some embodiments, a tissue sample comprises a portion of tissue taken from any internal organ, a cancerous, pre-cancerous, or non-cancerous tumor, skin, hair (including roots), eye, muscle, bone marrow, cartilage, white adipose tissue, or brown adipose tissue. In some embodiments, a fluid sample comprises buccal swabs, blood, cord blood, saliva, semen, urine, ascites fluid, pleural fluid, spinal fluid, pulmonary lavage, tears, sweat, and the like. Those of ordinary skill in the art will appreciate that, in some embodiments, a "sample" is a "primary sample" in that it is obtained directly from a source (e.g., a subject); in some embodiments, a "sample" is the result of processing of a primary sample, for example to remove certain potentially contaminating components and/or to isolate and/or purify certain components of interest.

In some embodiments, treatment with the compounds described herein results in gene expression patterns similar to those seen after anti-PD1 treatment. Programmed cell death protein 1 (PD1) is an immune checkpoint protein expressed by cells of the immune system, such as T and B lymphocytes. Additional immune checkpoint proteins include CTLA-4, BTLA, A2AR, B7-H3, B7-H4, IDO, LAG3, and TIM-3, among others. Immune checkpoint proteins generally function to dampen immune responses through regulation of T cell responses. As such, these proteins have been extensively targeted in cancer and autoimmunity research. Without wishing to be bound by theory, data herein demonstrate that the compounds described herein (e.g., exifone) and immune checkpoint inhibitors (e.g., anti-PD1 antibodies) may induce gene expression of similar pathways, such as genes involved in interferon responses.

The compounds disclosed herein can be administered in effective amounts to treat or prevent a disorder and/or prevent the development thereof in subjects. Treatment of a disease can refer to a reduction in disease symptoms to severity levels comparable to those prior to disease onset. In some embodiments, treatment may refer to a short-term (e.g., temporary and/or acute) and/or a long-term (e.g., sustained) reduction in disease symptoms. In some embodiments, treatment may refer to a remission of disease symptoms. Treatment of a disease may also refer to lessening or reduction of disease symptoms. In some embodiments, treating a subject comprises administering a composition to subject at risk of developing a disease in order to prevent disease development (e.g., prophylactic treatment). Prevention of disease development can refer to complete prevention of the symptoms of disease, a delay in disease onset, or a lessening of the severity of the symptoms in a subsequently developed disease Preferably, treatment with the compositions described herein results in an improvement or remediation of the symptoms of the disease or condition. The improvement is any improvement or remediation of the disease or condition, or symptom of the disease or condition. The improvement is an observable or measurable improvement, or may be an improvement in the general feeling of well-being of the subject.

In particular embodiments, treating or treatment results in "neuroprotection". As used herein, neuroprotection or "neuroprotective effects" refer to the preservation of neuronal structure or tissue architecture. In instances of insult (e.g. the presence of a neurological disorder), neuroprotection may refer to a reduction or slow in neuronal loss, restoration of neuronal function, or prevention of further neurodegeneration.

Administration of the disclosed compounds can be accomplished via any mode of administration for therapeutic agents. Administration can occur by injection, irrigation, inhalation, consumption, electro-osmosis, hemodialysis, iontophoresis, and other methods known in the art. In some embodiments, administration route is auricular, buccal, conjunctival, cutaneous, dental, endocervical, endosinusial, endotracheal, enteral, epidural, interstitial, intra-articular, intra-arterial, intra-abdominal, intraauricular, intrabiliary, intrabronchial, intrabursal, intracavernous, intracerebral, intracisternal, intracorneal, intracronal, intracoronary, intracranial, intradermal, intradiscal, intraductal, intraduodenal, intraduodenal, intradural, intraepicardial, intraepidermal, intraesophageal, intragastric, intragingival, intrahepatic, intraileal, intralesional, intralingual, intraluminal, intralymphatic, intramammary, intramedulleray, intrameningeal, instramuscular, intranodal, intraocular, intraomentum, intraovarian, intraperitoneal, intrapericardial, intrapleural, intraprostatic, intrapulmonary, intraruminal, intrasinal, intraspinal, intrasynovial, intratendinous, intratesticular, intrathecal, intrathoracic, intratubular, intratumoral, intratympanic, intrauterine, intravascular, intraventricular, intravesical, intravestibular, intravenous, intravitreal, larangeal, nasal, nasogastric, oral, ophthalmic, oropharyngeal, parenteral, percutaneous, periarticular, peridural, perineural, periodontal, respiratory, retrotubular, rectal, spinal, subarachnoid, subconjunctival, subcutaneous, subgingival, sublingual, submucosal, subretinal, topical, transdermal, transendocardial, transmucosal, transplacental, trantracheal, transtympanic, ureteral, urethral, and/or vaginal.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a Compound of the Invention and a pharmaceutically acceptable carrier, such as a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxy-propyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention relates to a pharmaceutical composition comprising a compound of Formula I or Formula II and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

In some embodiments, the compounds described herein may be assembled into a kit for therapeutic, research, or diagnostic uses. Specifically, such kits may include one or more compounds described herein, along with instructions describing the intended therapeutic application and the proper administration of the compounds. In certain embodiments compounds in a kit may be in a pharmaceutical formulation and dosage suitable for a particular application and for a method of administration of the agents. In some embodiments, the kit may further comprise a compound effective in treating a disease responsive to HDAC1 activation. In some embodiments the compound effective in treating a disease responsive to HDAC1 activity is selected from the group consisting of Aricept®, Exelon®, Razadyne®, Cognex® and Namenda®.

In further embodiments, compounds described herein are administered in combination with tests to monitor liver function through assessment of serum aminotransferase activity and other markers to improve safety. In some embodiments the liver test comprises a genetic test to determine liver metabolic enzyme genotypes to improve safety.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Definitions used in the following examples and elsewhere herein are:

Zinc chloride: $ZnCl_2$
Phosphorous oxychloride: $POCl_3$
Sodium bicarbonate: $NaHCO_3$ Example 1—Preparation of (2-fluoro-3,4-dihydroxyphenyl)(3,4,5 trihydroxyphenyl)methanone (IId)

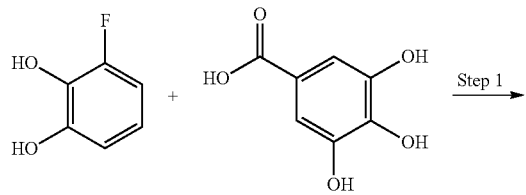

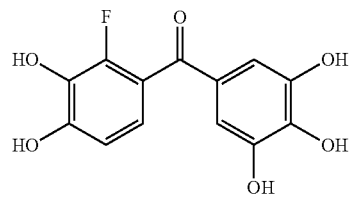

Step-1: (2-fluoro-3,4-dihydroxyphenyl)(3,4,5 trihydroxyphenyl)methanone (IId)

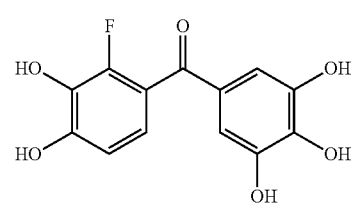

3,4,5-trihydroxybenzoic acid, 3-fluorobenzene-1,2-diol, anhydrous zinc chloride and phosphorous oxychloride were combined in a round bottom flask, stirred and heated to 80° C. for 2 hours. After cooling, the product was precipitated from the reaction mixture by addition of a mixture of water and ice. The product was washed with water, treated with a solution of sodium bicarbonate, washed again with water and finally recrystallized from aqueous solution to yield the desired product.

The following compounds of the invention can be made according to the procedure outlined above with the appropriate starting materials:

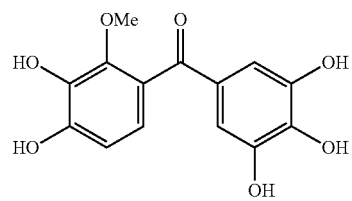

(3,4-dihydroxy-2-methoxyphenyl) (3,4,5-trihydroxyphenyl)methanone

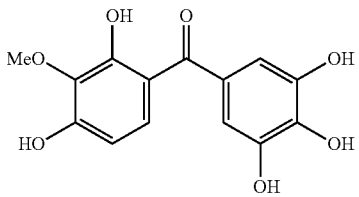

(2,4-dihydroxy-3-methoxyphenyl) (3,4,5-trihydroxyphenyl)methanone

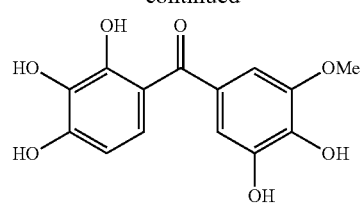

(3,4-dihydroxy-5-methoxyphenyl)
(2,3,4-trihydroxyphenyl)methanone

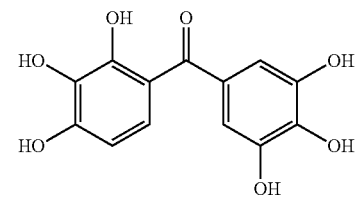

(2,3,4-trihydroxyphenyl)
(3,4,5-trihydroxyphenyl)methanone

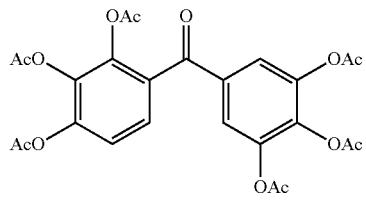

4-(3,4,5-triacetoxybenzoyl)benzene-
1,2,3,-triyl triacetate

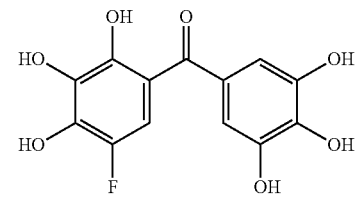

(5-fluoro-2,3,4-trihydroxyphenyl)
(3,4,5-trihydroxyphenyl)methanone

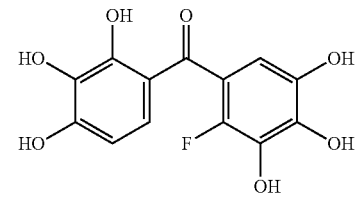

(2-fluoro-3,4,5-trihydroxyphenyl)
(2,3,4-trihydroxyphenyl)methanone

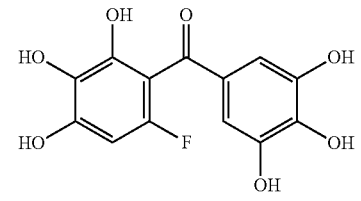

(6-fluoro-2,3,4-trihydroxyphenyl)
(3,4,5-trihydroxyphenyl)methanone

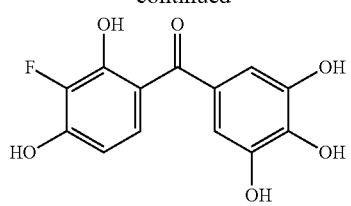

(3-fluoro-2,4-dihydroxyphenyl)
(3,4,5-trihydroxyphenyl)methanone

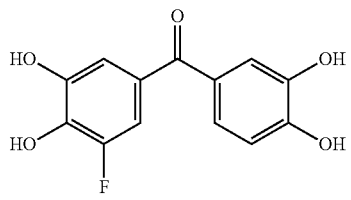

(3,4-dihydroxyphenyl)(3-fluoro-
4,5-dihydroxyphenyl)methanone

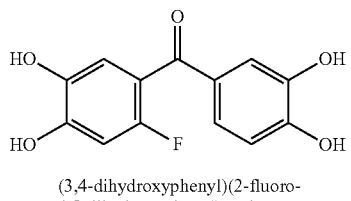

(3,4-dihydroxyphenyl)(2-fluoro-
4,5-dihydroxyphenyl)methanone

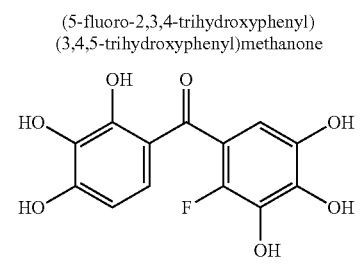

(3-fluoro-4,5-dihydroxyphenyl)
(2,3,4-trihydroxyphenyl)methanone

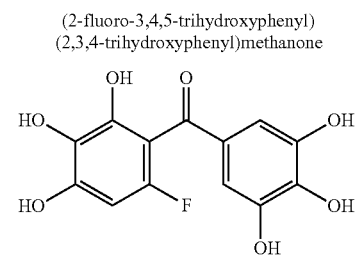

(4-fluoro-2,3-dihydroxyphenyl)
(3,4,5-trihydroxyphenyl)methanone

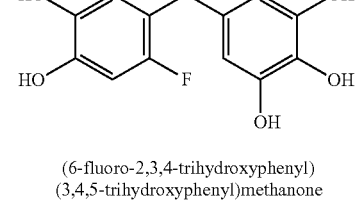

(4-fluoro-3,5-dihydroxyphenyl)
(2,3,4-trihydroxyphenyl)methanone

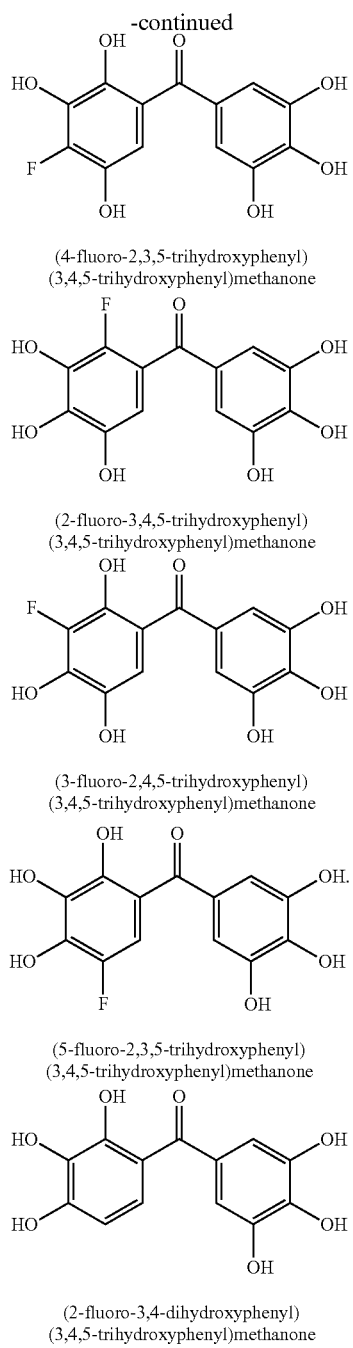

(4-fluoro-2,3,5-trihydroxyphenyl)
(3,4,5-trihydroxyphenyl)methanone (2-fluoro-3,4,5-trihydroxyphenyl)
(3,4,5-trihydroxyphenyl)methanone (3-fluoro-2,4,5-trihydroxyphenyl)
(3,4,5-trihydroxyphenyl)methanone (5-fluoro-2,3,5-trihydroxyphenyl)
(3,4,5-trihydroxyphenyl)methanone (2-fluoro-3,4-dihydroxyphenyl)
(3,4,5-trihydroxyphenyl)methanone Example 2—RapidFire Mass Spec Assay for Histone Deacetylases Bio-H4K12ac and Bio-p53K382ac peptides were purchased from Anaspec (Fremont, Calif.). Recombinant HDAC1 and HDAC2 were from BPS Biosciences (San Diego, Calif.). Biochemical assays for evaluation of enzyme activity were performed in 384-well microplates (Perkin Elmer, Waltham, Mass.). A high throughput mass spectrometry assay based on RapidFire™ platform (Agilent Technology, Wakefield, Mass.) was used for analysis of HDAC activity with acetylated peptide substrates derived from histone Bio-H4K12ac (Anaspec #64849) and non-histone Bio-p53K382ac (Anaspec #65046) sequences.

For determination of dose dependence curves, test compounds were preincubated with HDAC1 for 15 minutes. Histone deacetylase reactions were performed following addition of acetylated peptide substrate. The reactions were performed in standard 384-well plates in 50 μl volume with an assay buffer containing 50 mM Tris, pH 7.4, 100 mM KCl, and 0.01% Brij-35. Enzyme reactions were terminated by adding 5 μl of 10% formic acid. Experiments designed to determine the mechanism of action used a varied range of substrate and test compound concentrations. For determining the dose response of individual compounds, HDAC1 reactions were performed with 1 μM of the acetylated peptide substrate for durations ranging from 45 mins for Bio-p53K382ac and 60 minutes for Bio-H4K12ac, with the aim of keeping the substrate conversion below 10%.

For Mass Spec based detection, assay plates were transferred onto a high throughput RapidFire200 integrated autosampler/solid-phase extraction (SPE) system (Agilent Technologies, Wakefield, Mass.) coupled to an API4000 triple quadrupole mass spectrometer (Applied Biosystems, Concord, Ontario, Canada). Additional details for the RapidFire MS analysis are described elsewhere (Rye et al. Advances in label-free screening approaches for studying sirtuin-mediated deacetylation. J Biomol Screen. 2011 December; 16(10):1217-26; Rye et al. Advances in label-free screening approaches for studying histone acetyltransferases. J Biomol Screen. 2011 December; 16(10):1186-95). The peaks detected by Mass Spec were integrated and processed with RapidFire peak integration software (Agilent).

Percentage of substrate conversion was estimated from the RapidFire HTMS assay as a function of product and substrate mass spectrum peak areas and is equal to 100*[Product/(Product+Substrate)]. Percentage of enzyme activation=[(MIN-test compound)/(MIN−MAX)*100], where MINimal (0%) enzyme activity is observed in the presence of a histone deacetylase inhibitor [10 μM SAHA (suberoylanilide hydroxamic acid), SAHA; Vorinostat] and MAXimal enzyme activity of HDAC1 reaction in absence of test compound as 100% activity. MAX and MIN values were calculated from an average of 16 wells of a single column of 384 well plate. Data were analyzed and plotted using Graphpad Prism 6.

Activator potencies were compared by estimating the $EC^{1.5}$ values as a function of EC50 values and maximum relative velocity ($RV_{max}$) (Dai et al, 2010). $EC^{1.5}$ is the concentration of the activator required to achieve 1.5 fold activation (Dai et al, 2010). Data on enzyme activation were analyzed using non-essential enzyme activation (Segel, (1975) Enzyme Kinetics, John Wiley, New York).

Example 3—Animals and Behavioral Tests 8-month-old males (WT or 5XFAD mice) received daily for two weeks of full treatment either vehicle (80% saline, 10% DMSO, 10% Tween-80) or exifone (FIG. 1A) (50 mg/kg). Administration was by intraperitoneal injection for 2 weeks. After 2 weeks of treatment, mice were handled more than 3 days before each behavioral test.

Open field test was monitored by TSE Multi Conditioning System, total distance traveled and the number of visits in center were measured using automated activity monitors.

To assess memory formation, fear-conditioning tests in rodents were used. In these paradigms, the extent of freezing behavior, which is defined as the complete lack of movement other than from respiration upon re-exposure to an aversive stimulus (e.g. mild foot shock) and an environmental cue in the form of a specific context (e.g. test chamber) or cue (e.g. a tone), provides an assessment of the strength of memory. In contextual fear conditioning, rodents exhibiting freezing behavior upon re-exposure to the context of the test chamber are considered to have formed an associative memory. In cued fear conditioning, rodents exhibiting freezing behavior upon re-exposure to an auditory stimulus in a modified test chamber are considered to have formed an associative memory. Whereas contextual fear conditioning is known to be largely dependent upon hippocampal function, in contrast, cued fear conditioning is known to be largely dependent upon the function of the amygdala in combination with the hippocampus under certain conditions.

For contextual fear conditioning, mice were put in the conditioning chamber (TSE systems) for 3 min, after which they received a one-time footshock (2 s, 0.8 mA). After 24 hr in the home cage, mice were placed in the same chamber and the freezing bouts, defined as a total lack of movement except for a heartbeat and respiration, were scored during every 10 s during a 3 min period.

Cued fear conditioning was performed by placing the animals in the test chamber for 3 min following exposure to the auditory cue (30 s, 20 kHz, 75 db sound pressure level) and a foot shock (2 s, 0.8 mA). Associative learning was assessed 24 hr later by placing the mice in the modified chamber and delivery of the identical auditory cue for 3 min.

Example 4—Exifone is a Potent Small Molecule Activator of HDAC1

Figure 1B:
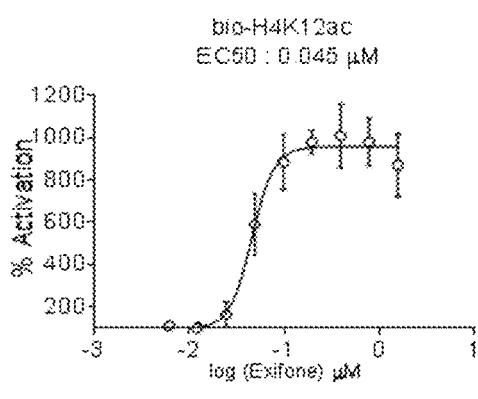
Figure 1C:
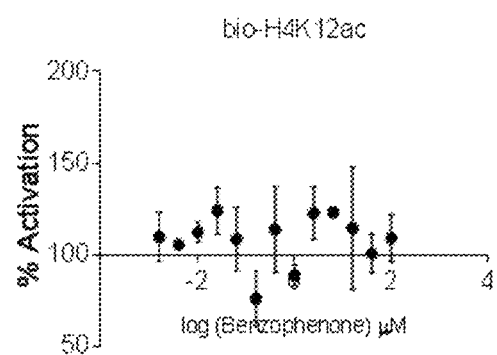
Figure 1D:
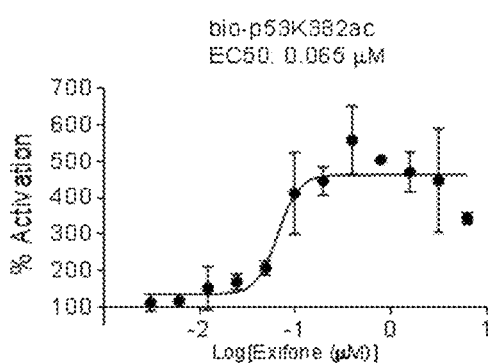
Figure 1E:
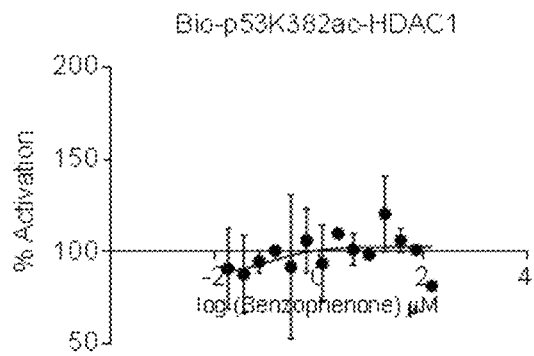

Using RapidFire Mass Spec assay with a histone tail peptide (Bio-H4K12ac) substrate, we demonstrate that Exifone (FIG. 1A) acts as a small molecule activator of HDAC1. Histone tail peptides bio-H2K12ac (FIGS. 1B and 1C) and bio-p53K382ac (FIGS. 1D and 1E) were used as substrates to measure HDAC1 activation in the presence of exifone (FIGS. 1B and 1D) or bezophenone (FIGS. 1C and 1E). The data demonstrate a dose-dependent increase in HDAC1 activation in the presence of exifone. Exifone shows an EC50 value of 0.045 µM, with maximal activation values that reach up to nine fold (with 2 hour incubation of the HDAC1 at room temperature prior to addition to reaction mix) (FIGS. 1B and 1D). Benzophenone is a structurally simpler compound that lack the six hydroxyl groups found in exifone (FIG. 1A) and did not cause HDAC1 activation (FIGS. 1C and 1D).

Figure 2:
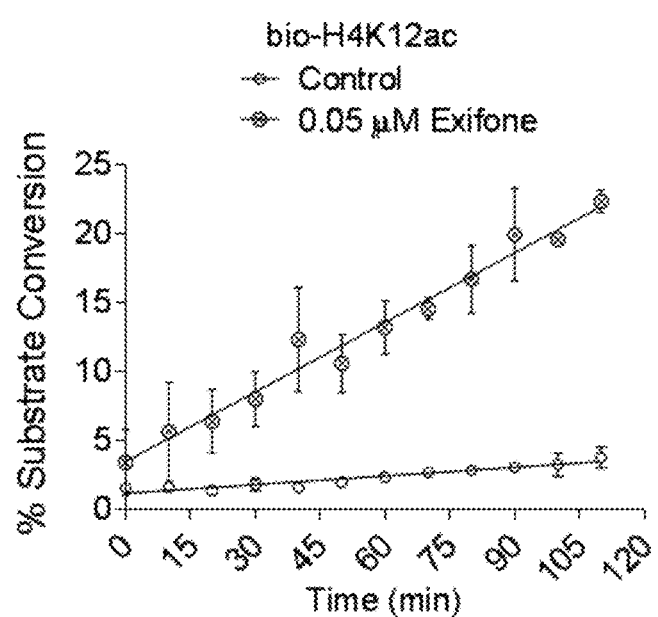
FIG. 2 shows that exifone increases the rate of deacetylation reaction by HDAC1 as observed via monitoring the percentage of substrate conversion.
Figure 4:
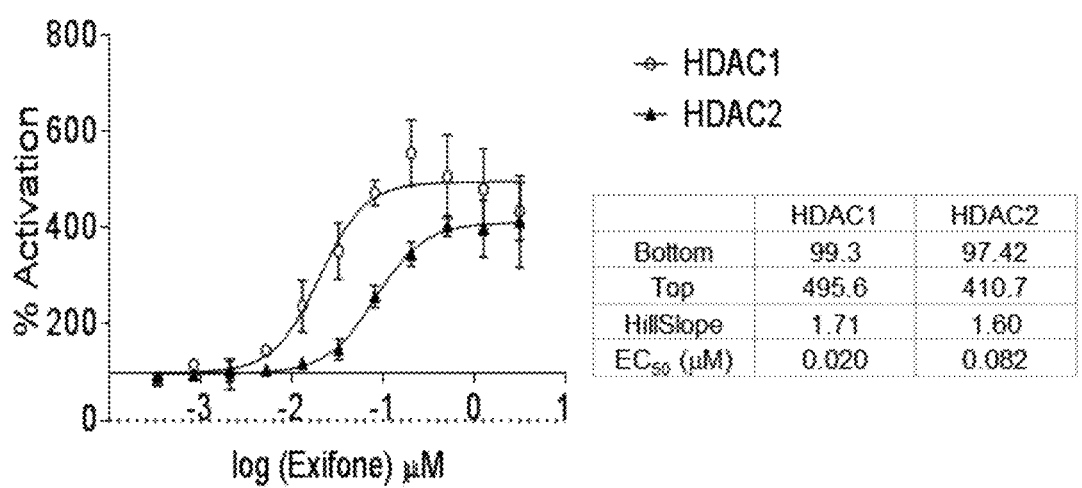
FIG. 4 illustrates the selectivity of exifone towards HDAC1 activation.

Further, exifone increased the rate of HDAC1-mediated deacetylation reactions (FIG. 2). The rate of substrate conversion of bio-H2K12ac (1 µM) by HDAC1 (40 nM) in the presence (0.05 µM) and absence (control) of exifone. As shown in FIG. 2, exifone increased the rate of HDAC1-mediated reactions compared to control conditions. Exifone was also at least four fold more selective for HDAC1 activation, as compared with that of HDAC2. The observed EC50 value for HDAC1 was 0.02 µM compared to 0.082 µM for HDAC2 (FIG. 4).

Exifone partially reversed the inhibitory effect of the benzamide HDAC inhibitor, CI-994, in a dose dependent manner (FIG. 3). Preincubation of HDAC1 for 15 minutes with 1 µM or 10 µM exifone resulted in HDAC1 activation at lower concentrations of CI-994 (FIG. 3A). Further, a dose-dependent increase of HDAC1 activity was observed even when HDAC1 was preincubated for 2 hours with 1 µM, 5 µM, or 10 µM CI-994 (FIG. 3B and FIG. 3C).

Figure 5A:
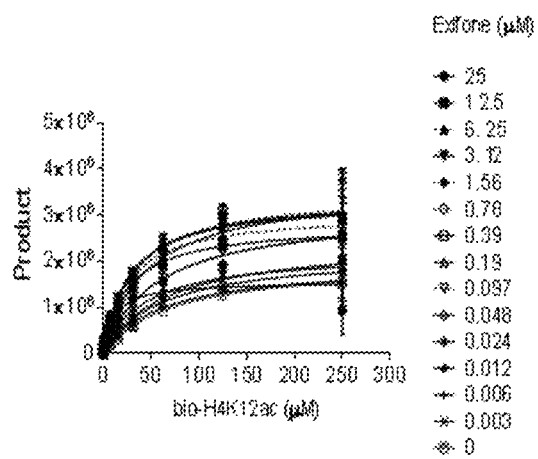
FIGS. 5A-5D illustrate the reaction mechanism of HDAC1 activation by exifone as determined by varying concentrations of both substrate and activator.
Figure 5B:
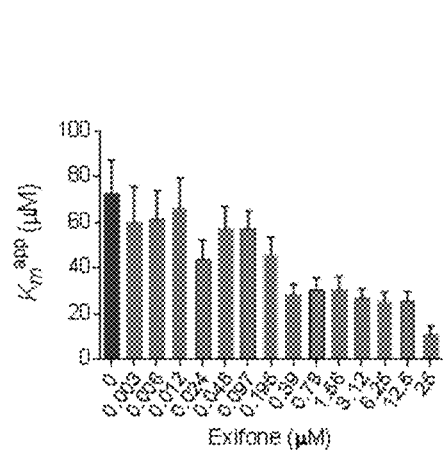
Figure 5C:
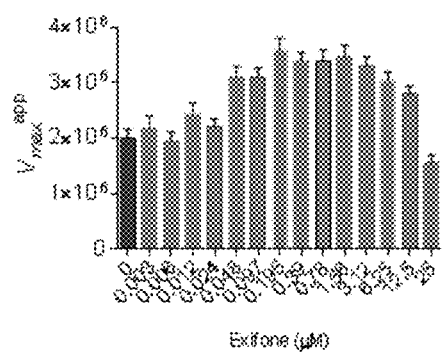
Figure 5D:
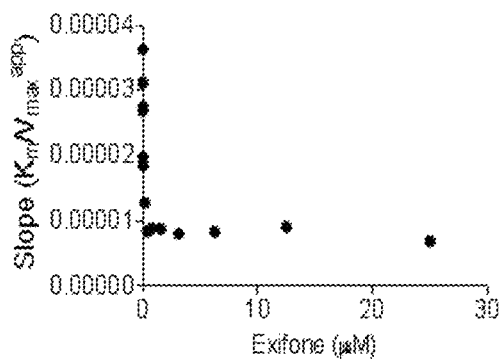
Figure 6:
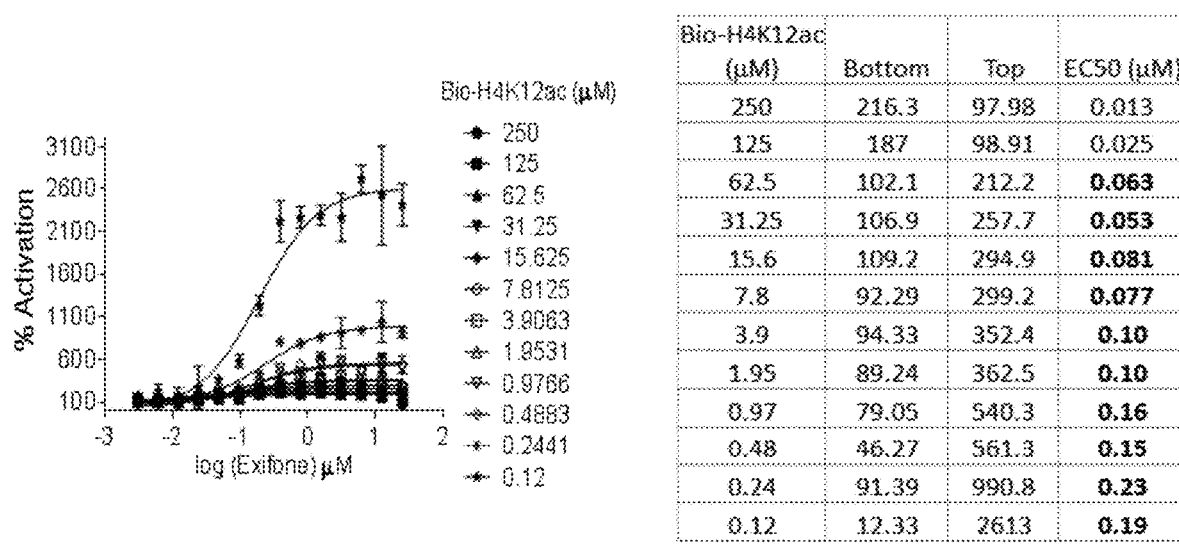
FIG. 6 shows the dose dependent activation of HDAC1 by exifone at variable substrate concentrations of an acetylated histone substrate (Bio-H4K12ac).

The mechanism of exifone-mediated HDAC1 activation was determined by varying the concentrations of the substrate (bio-H4K12ac) and activator (exifone). Increasing exifone concentrations decreased the apparent $K_m$ for the bio-H4K12ac peptide (FIG. 5B) and also increased the $V_{max}$ (FIG. 5C). Replot of the slope (ratio of $K_m/V_{max}$) vs. exifone concentration resulted in a descending hyperbolic curve (FIG. 5D). The mechanism of action was consistent with that of a mixed non-essential reaction. Dose-dependent, exifone-mediated activation of HDAC1 was also observed at variable substrate concentrations of bio-H4K12ac (FIG. 6). The highest level of activation was observed when the substrate concentration was significantly lower that the $K_m$ value ($[5]<<[K_m]$). No activation was observed at peptide concentrations of 125 and 250 µM.

Figure 7:
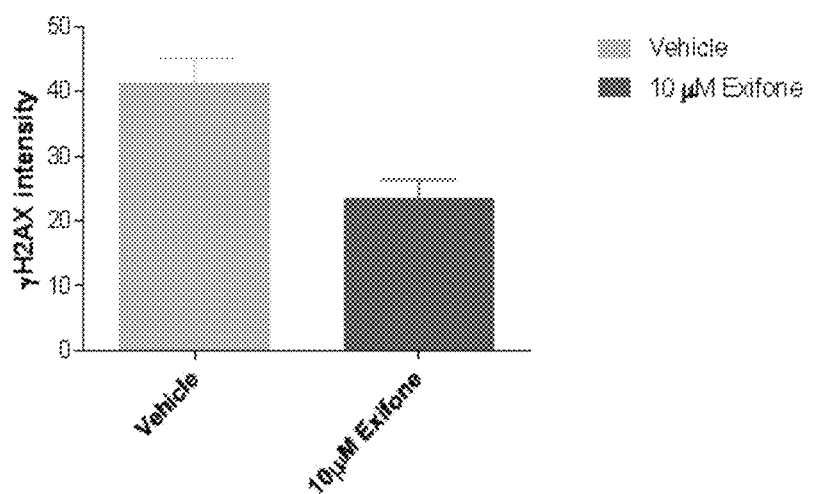
FIG. 7 shows that exifone treatment of neurons results in protection from DNA damage.

Further, immunostaining for γH2AX, a marker of DNA double-stranded breaks, in cultured neurons demonstrated that treatment with exifone significantly reduced the intensity of γH2AX. These data provided evidence for the role of exifone in providing protection from DNA damage (FIG. 7).

Moreover, systemic administration of exifone in AD mice model (CK-p25 mice) significantly ameliorated neuronal loss (FIG. 8) and enhances the cognitive function in a contextual fear-conditioning test, indicating a restoration of hippocampal memory, but not in cued fear-conditioning test, without an effect on basal locomotion in the open-field-test (FIG. 9).

The above results using polyhydroxylated benzophenone exifone demonstrate the potential of HDAC1 activation as a neuroprotective strategy to target Alzheimer's disease and memory-related disorders where hippocampal function is disrupted.

Figure 10A:
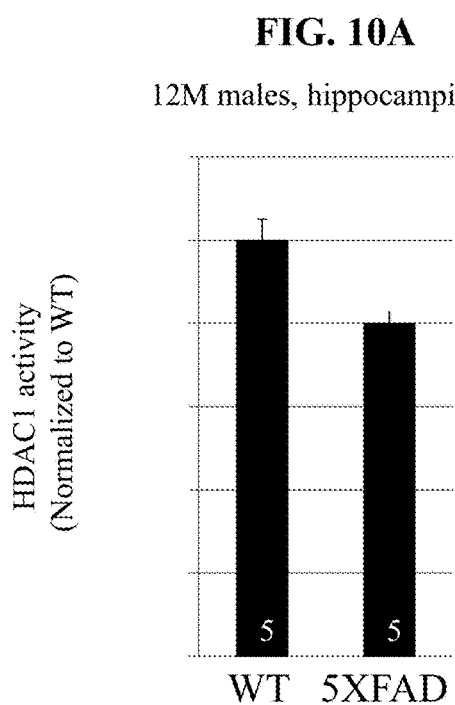
FIGS. 10A-10C demonstrate exifone activation of HDAC activity in vivo.

Example 5—Exifone Treatment Reinstates Memory Deficits in Neurodegenerative Mouse Models To determine the potential of exifone use in the treatment of neurodegenerative diseases, HDAC1 activity was assessed in the 5XFAD mouse model of AD. Hippocampi from 12-month-old 5XFAD mice or age-match controls were homogenized in IP buffer. Lysates were immunoprecipitated with anti-HDAC1 (Abcam, ab7028). Endogenous HDAC1-bound beads were analyzed for histone deacetylase activity using FLUOR DE LYS® HDAC fluorometric activity assay kit (Enzo) according to the manufacturer's instructions. Histone deacetylase activity was normalized to input HDAC1 protein levels which were analyzed by western blot. Interestingly, we observed that the activity of HDAC1 was impaired in 5XFAD mouse brain compared to wild type (WT) controls (FIG. 10A).

Figure 10B:
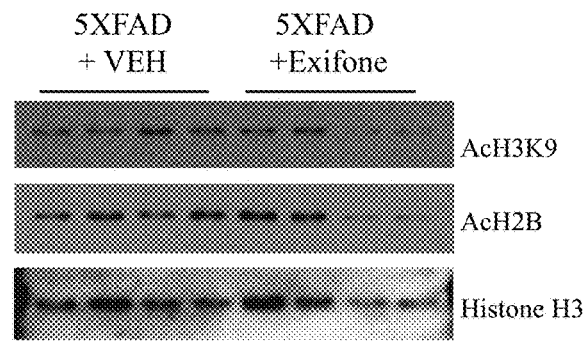
Figure 10C:
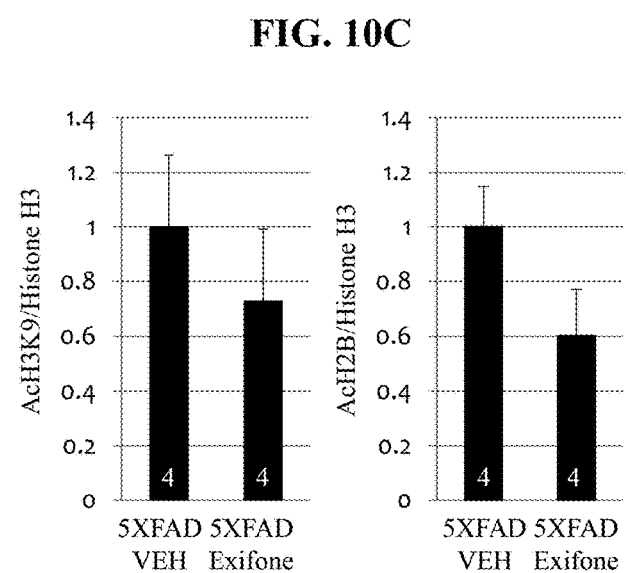

To determine the effects of restoration of HDAC1 activity in 5XFAD mice, mice were treated with exifone. Briefly, eight-month-old mice were administered doses of 50 mg/kg body weight exifone or vehicle control (10% DMSO, 10% Tween-80 and 80% saline) by intraperitoneal injection for 2 weeks. After 2 weeks of treatment, hippocampi were dissected and homogenized in RIPA buffer for Western blotting (FIGS. 10B and 10C). These results demonstrate a trend towards increased histone deacetylation and HDAC1 activity in 5XFAD mice treated with exifone.

Figure 11:
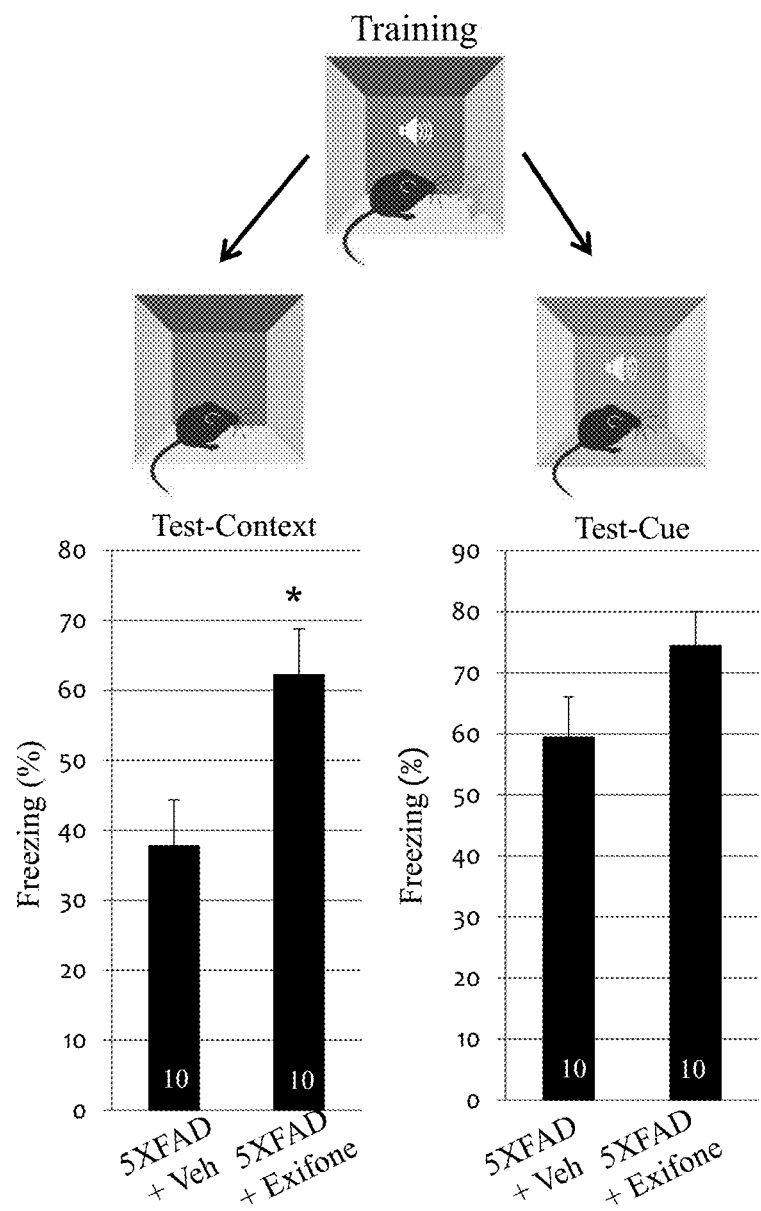
FIG. 11 displays a schematic of context and cued behavior tests and results of exifone administration to the AD mouse model.

Behavioral tests were performed on vehicle treated wild type (WT) mice and 5XFAD mice treated with either vehicle control or exifone. Eight-month-old mice were administered doses of 50 mg per kg body weight exifone or vehicle by intraperitoneal injection for 2 weeks, and then subject to fear conditioning test as described in Example 3. Mice were put in the conditioning chamber for 3 min, and then cue (sound) was applied for 30 seconds right before a one-time, 2 second, foot-shock. One day later, mice were re-exposed to the training context for 3 min without cue to address contextual fear memory. The following day, mice were exposed to a novel chamber, and then cue was applied for 3 min. See diagram in FIG. 11. In both contexts, freezing behavior of the mice was scored for examination memory.

Total distance traveled (FIG. 9A) and number of visits to the center (FIG. 9B) were analyzed during open-field tests. Exifone treatment had no effect on either of these parameters, indicating no confounding effects of exifone on locomotion. The freezing responses of the mice in conditioned (FIG. 9C) and cued (FIG. 9D) fear conditioning tests were significantly increased in exifone-treated 5XFAD mice. These data demonstrate that administration of exifone enhanced associated memory and thus prevented cognitive decline in 5XFAD mice (FIG. 9).

Figure 12A:
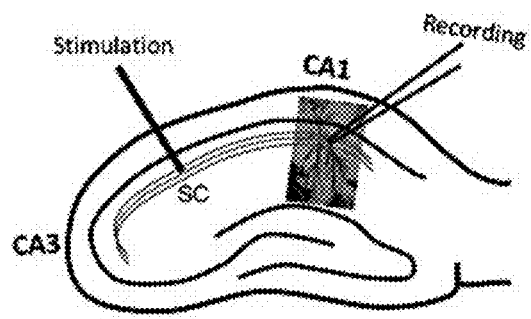
FIGS. 12A-12B display results of exifone administration on LTP induction.
Figure 12B:
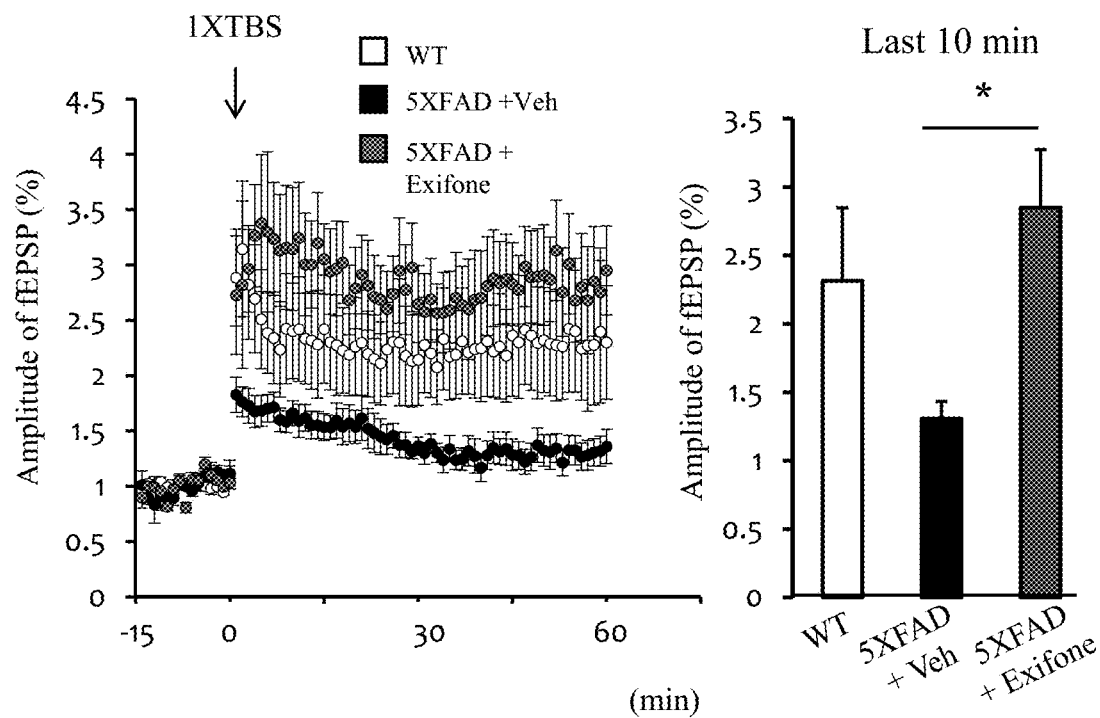

Thirteen-month-old mice were administered doses of 50 mg per kg body weight exifone or vehicle by intraperitoneal injection for 2 weeks before long-term potentiation (LTP) recordings. For LTP recording, mice were anesthetized with isoflurane and decapitated. Transverse hippocampal slices (400 μm thick) were prepared in ice-cold dissection buffer (in mM: 211 sucrose, 3.3 KCl, 1.3 NaH2PO4, 0.5 CaCl2, 10 MgCl2, 26 NaHCO3 and 11 glucose) using a Leica VT1000S vibratome (Leica). Slices were recovered in a submerged chamber with 95% $O_2$/5% $CO_2$-saturated artificial cerebrospinal fluid (ACSF) consisting of (in mM) 124 NaCl, 3.3 KCl, 1.3 NaH2PO4, 2.5 CaCl2, 1.5 MgCl2, 26 NaHCO3 and 11 glucose for 1 h at 28-30° C. For extracellular LTP recording, CA1 field potentials evoked by Schaffer collateral stimulation with bipolar electrode was measured every 30 s. After recording of stable baseline for 15 min, LTP was induced by single theta-burst stimulations (TBS, containing 10 brief bursts which consisted of four pulses at 100 Hz). Treatment of 5XFAD mice with exifone resulted in the reinstatement of LTP induction (FIG. 12B).

Figure 8A:
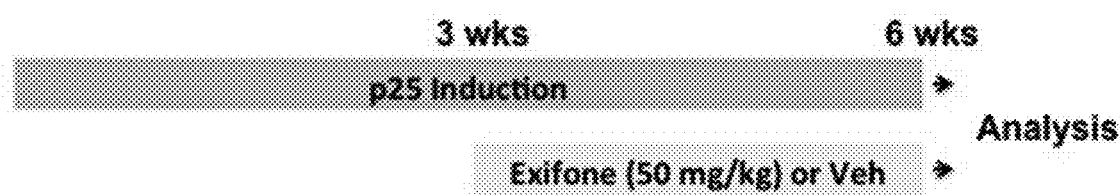
FIGS. 8A-8C show that exifone treatment ameliorates neuronal loss and cognitive decline in CK-p25 mice.
Figure 8B:
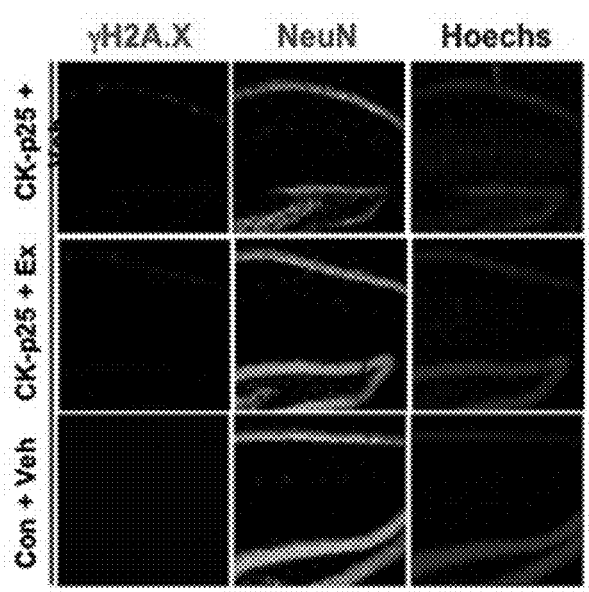

Similar effects were observed in an inducible mouse model of forebrain-specific neurodegeneration using CK-p25 mice. CK-p25 mice are characterized by massive neuronal loss and severe memory impairment after 6 weeks of the p25 transgene induction (Cruz et al. Aberrant Cdk5 activation by p25 triggers pathological events leading to neurodegeneration and neurofibrillary tangles. Neuron. 2003 Oct. 30; 40(3):471-83). Exifone was chronically administered in CK-p25 mice, model, 3-month-old CK-p25 mice and control mice (no p25 overexpression) were induced for 6 weeks. They received either daily Exifone or vehicle for 3 weeks from week 3 to 6 during the induction period (FIG. 8A). Using immunohistochemistry, elevated DNA damage, as revealed by increased γH2A.X positive neurons, and profound neuronal loss, as revealed by reduced NeuN and Hoechst staining intensity in the hippocampus of CK-p25 mice, was observed. Treatment with exifone resulted in in significant reduction of these markers of neurodegeneration (FIG. 8B).

Figure 8C:
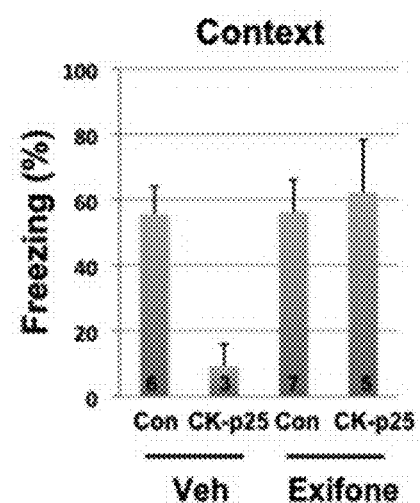
Figure 9A:
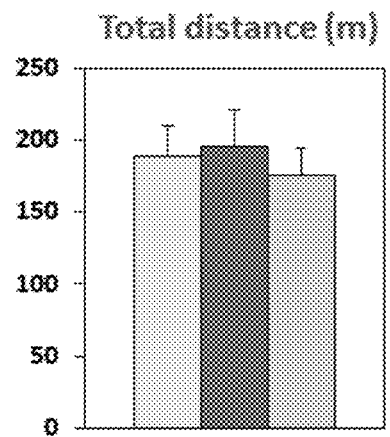
FIGS. 9A-9D display results of exifone administration to the AD mouse model.
Figure 9B:
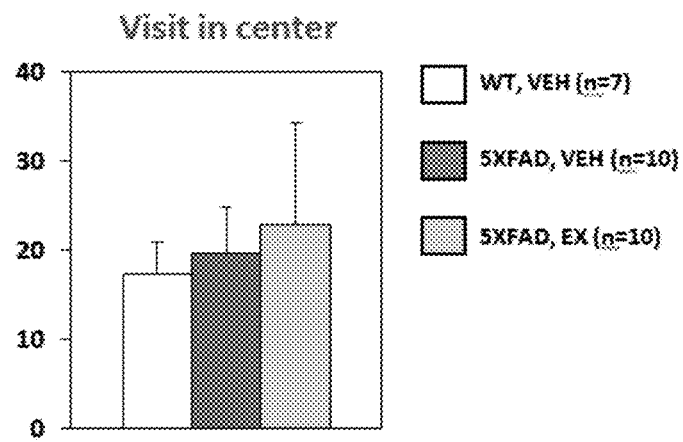
Figure 9C:
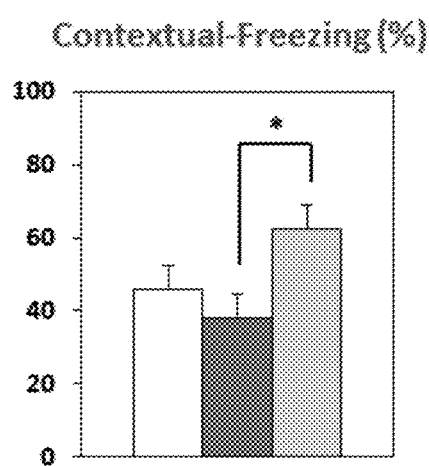
Figure 9D:
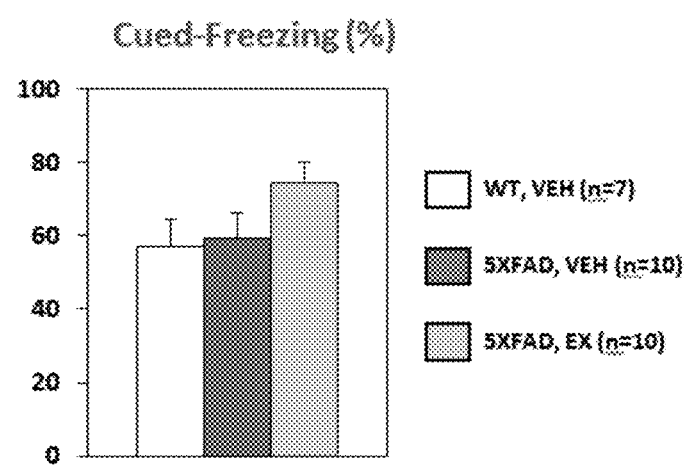

The associative memory in mice was examined by the contextual fear conditioning test described in Example 3. Mice were treated with vehicle control or exifone and freezing behavior observed 24 hours after contextual fear conditioning training. The freezing behavior of CK-p25 mice treated with vehicle control was markedly reduced compared to vehicle-treated control mice. However, CK-p25 mice that received exifone treatment demonstrated comparable freezing behavior to vehicle-treated or exifone-treated control mice (FIG. 8C). These data demonstrate that the neurodegeneration phenotype in CK-p25 mice was significantly ameliorated by Exifone treatment (FIG. 8B and FIG. 8C).

Figure 15A:
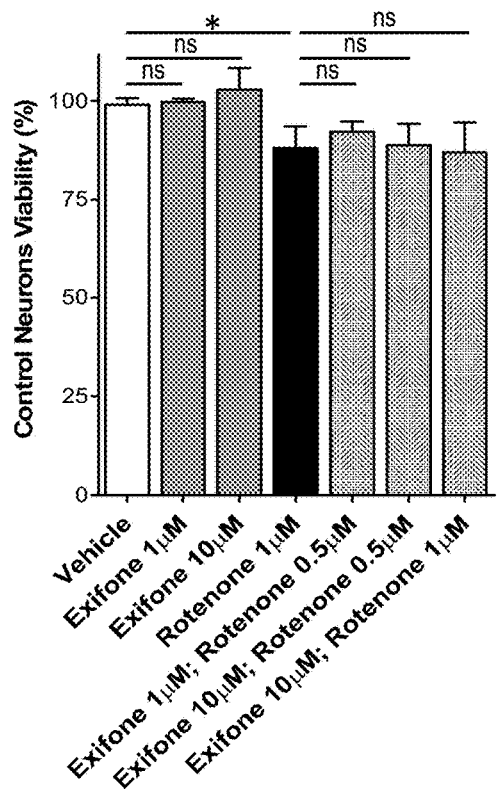
FIGS. 15A-15B display the results of exifone treatment in a human iPSC model of neurodegeneration with mutations in the microtubule-associated protein tau and exposure to mitochiondrial stress.
Figure 15B:
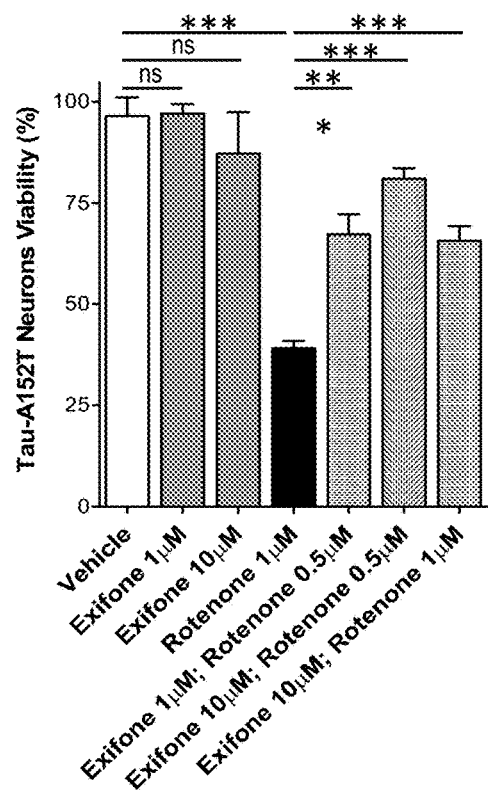

To further determine the effects of exifone on neurodegenerative disorders like frontotemporal dementia, Alzheimer's disease, and Parkinson's disease, a cellular model of mitochondrial dysfunction and tauopathy was used. Human induced pluripotent stem cell (iPSC)-derived neurons from a healthy control (FIG. 15A) and a frontotemporal dementia patient with a mutation in tau (FIG. 15B) were differentiated in culture for eight weeks (See Silva et al., Stem Cell Reports, 2016). Cultures were then pre-treated for 8 hours with exifone, followed by 18 hour treatment with the mitochondrial and oxidative stressor, rotenone, at varying concentrations. 1 μM of rotenone had no effect on the viability of healthy control neurons (FIG. 15A, black bar). However, the tauopathy patient-derived neurons showed enhanced vulnerability to rotenone, resulting in a >50% decrease in viability (FIG. 15B, black bar). Exifone treatment at multiple doses rescued the vulnerability of the tauopathy patient-derived neurons to rotenone-induced stress. Cell viability was measured by Alamar Blue (4 h) assay±SD. Statistical Analysis: Student T-Test; $^{ns}P>0.05$, *$P<0.05$, $P<0.01$, *$P<0.001$; n=2 and technical triplicates.

Figure 13A:
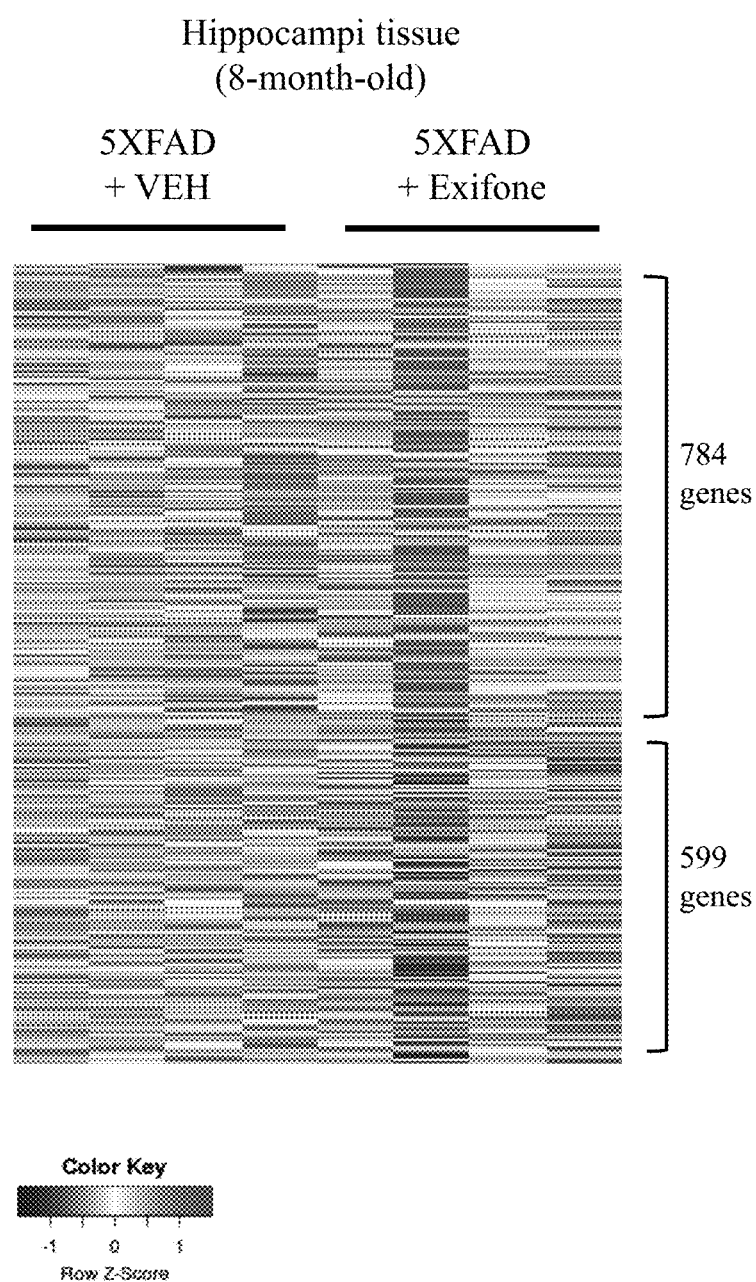
FIGS. 13A-13C display RNA-Seq results from 5XFAD mice treated with vehicle control or exifone and the results of gene enrichment analyses.

Example 6—Exifone Upregulates Gene Expression of Immune and Neurogenesis Pathways To determine the mechanisms of exifone action in neurodegeneration, genome-wide transcriptomic analyses were performed. Eight-month-old mice were administered doses of 50 mg/kg of exifone or vehicle by intraperitoneal injection for 2 weeks. After two weeks of administration, total RNA was extracted from hippocampi using TRIzol. Purified mRNA was used for RNA-seq library preparation using the BIOO NEXTflex kit (BIOO 5138-08) according to the manufacturer's instructions. Total mRNA (1 g) was subject to a sequential workflow of poly-A purification, fragmentation, first strand and second strand synthesis, DNA end-adenylation, and adaptor ligation. The libraries were enriched by 15 cycles of PCR reactions and cleaned with Agencourt AMPure XP magnetic beads (Beckman Coulter). The bar-coded libraries were equally mixed for sequencing in a single lane on the Illumina HiSeq 2000 platform at the MIT BioMicro Center. Thresholds for differential gene expression were set to a p-value of <0.05. RNA-Seq results revealed that exifone treatment resulted in the differential expression of 1,383 genes, of which 784 were upregulated and 599 were downregulated after exifone treatment (FIG. 13A).

Figure 13B:
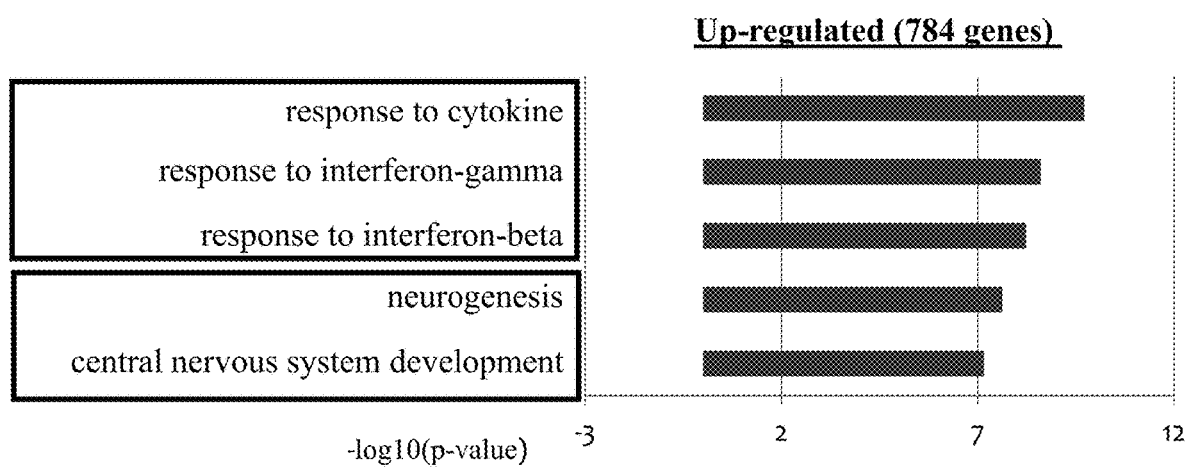
Figure 13C:
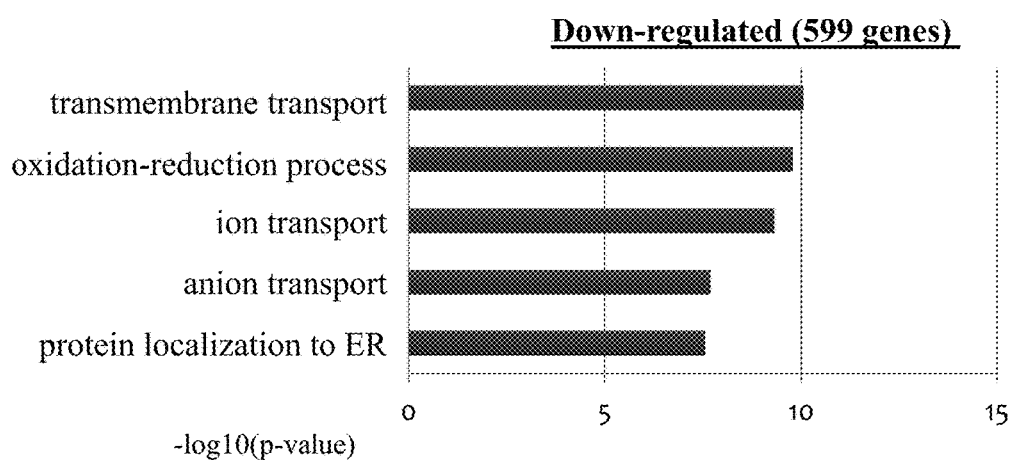
Figure 14A:
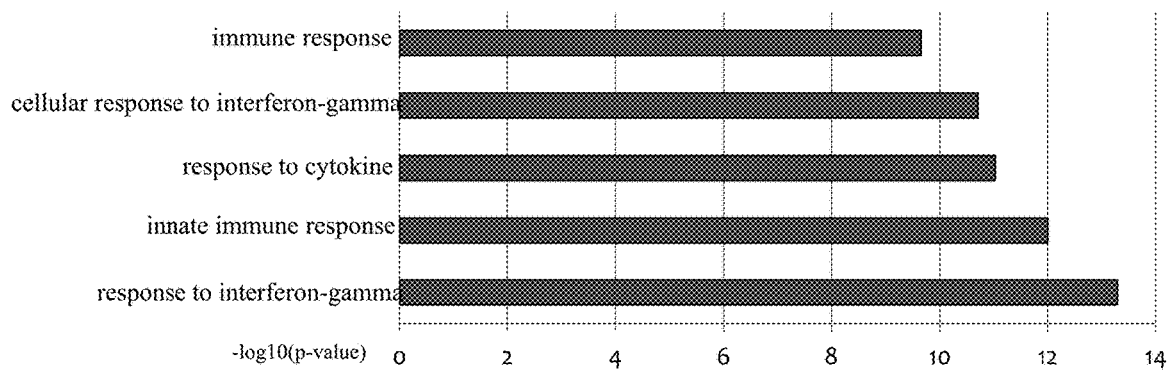
FIGS. 14A-14B display gene enrichment analyses of upregulated genes after anti-PD1 and exifone treatment.
Figure 14B:
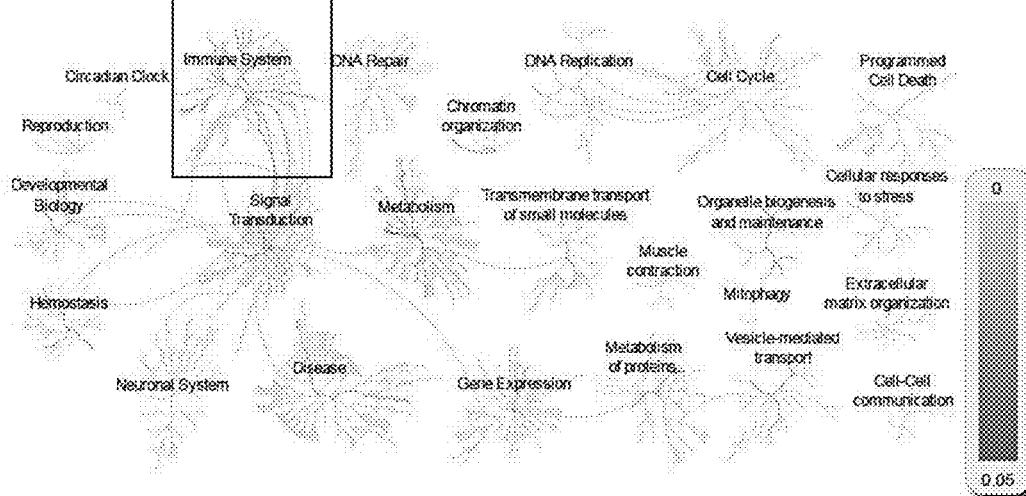

Enrichment analyses for gene lists were then performed using ToppGene Suite. These analyses demonstrated that the genes upregulated by exifone treatment were enriched for those involved in cytokine responses (e.g. responses to interferon (IFN)-β and IFN-γ), central nervous system development, and neurogenesis pathways (FIGS. 13B and 13C). These results were similar to those observed in an antibody-blockade of the immune checkpoint inhibitor, PD-1, in 5XFAD mice (Baruch et al., Nature Medicine, 22(2), 2016, pp. 135-139). Genes upregulated by exifone were then compared to those upregulated by anti-PD1 treatment, and a subsequent enrichment analysis was performed on the overlapping gene set (Anti-PD1_UP & Exifone_UP, FIG. 14A). The overlapping genes were significantly enriched in the same categories observed for exifone treatment. Additional data using Reactome analysis showed that IFN-γ was the most significantly enriched pathway (FIG. 14B), indicating that exifone may function similarly to PD-1.

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A prodrug of a compound of formula I:

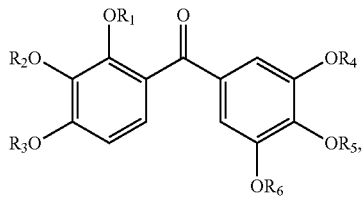

or a pharmaceutically acceptable salt, hydrate, solvate, or tautomer thereof, wherein:

$R_1$, $R_2$, $R_3$, $R_4$, $R_5$ and $R_6$ are each independently H, $PO(OR_x)_2$, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), CO(heteroaryl), $CON(R_y)_2$, $COO(C_1$-$C_6$ alkyl), $COO(C_2$-$C_6$ alkenyl), $COO(C_2$-$C_6$ alkynyl), $COO(C_3$-$C_8$ cycloalkyl), COO(3 to 8-membered heterocyclyl), or COO(aryl), COO(heteroaryl) wherein each $PO(OR_x)_2$, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), CO(heteroaryl), $CON(R_y)_2$, $COO(C_1$-$C_6$ alkyl), $COO(C_2$-$C_6$ alkenyl), $COO(C_2$-$C_6$ alkynyl), $COO(C_3$-$C_8$ cycloalkyl), COO(3 to 8-membered heterocyclyl), COO(aryl) or COO(heteroaryl) is optionally substituted with one or more substituents selected from the group consisting of halogen, OH, $NH_2$, CN, $C_1$-$C_6$ alkyl, aryl, heteroaryl and $C_1$-$C_6$ alkoxy;

$R_x$ is independently H, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) wherein each $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) is optionally substituted with one or more substituents selected from the group consisting of halogen, OH, $NH_2$, CN, $C_1$-$C_6$ alkyl, aryl, heteroaryl and $C_1$-$C_6$ alkoxy;

$R_y$ is independently H, $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) wherein each $C_1$-$C_6$ alkyl, $C_2$-$C_6$ alkenyl, $C_2$-$C_6$ alkynyl, $C_3$-$C_8$ cycloalkyl, 3 to 8-membered heterocyclyl, aryl, heteroaryl, $CO(C_1$-$C_6$ alkyl), $CO(C_2$-$C_6$ alkenyl), $CO(C_2$-$C_6$ alkynyl), $CO(C_3$-$C_8$ cycloalkyl), CO(3 to 8-membered heterocyclyl), CO(aryl), or CO(heteroaryl) is optionally substituted with one or more substituents selected from the group consisting of halogen, OH, $NH_2$, CN, $C_1$-$C_6$ alkyl, aryl, heteroaryl and $C_1$-$C_6$ alkoxy provided that the prodrug is not:

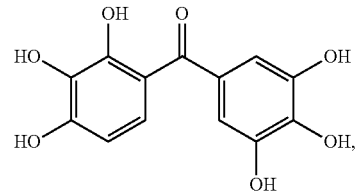

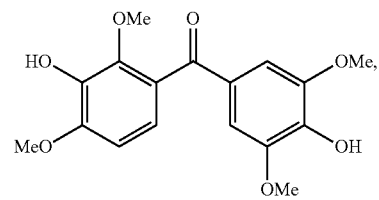

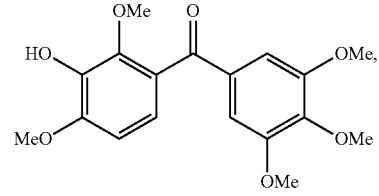

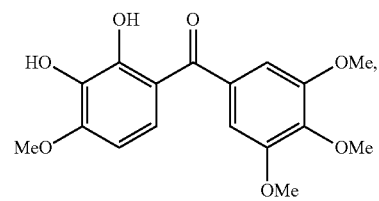

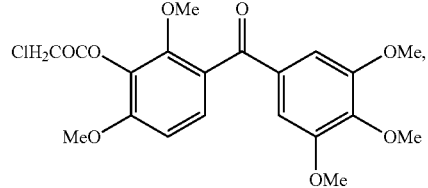

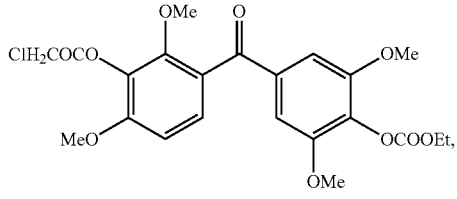

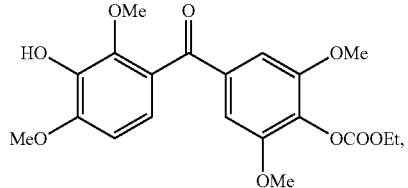

-continued

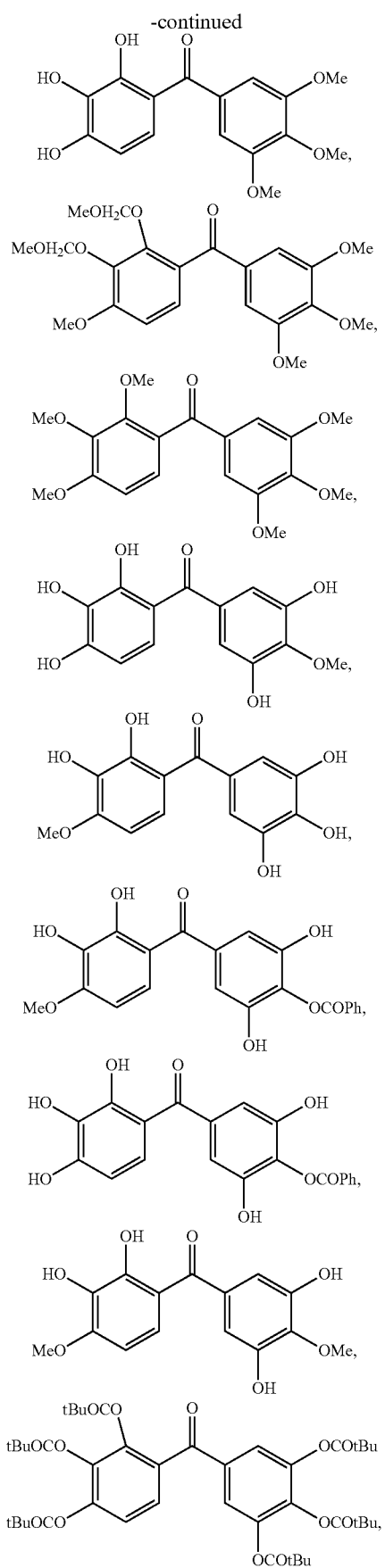

-continued

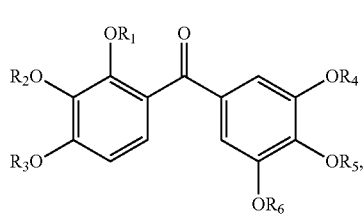

2. The prodrug of claim 1, or a pharmaceutically acceptable salt, hydrate, solvate, or tautomer thereof, wherein the compound has the formula Ia:

$$\text{Ia}$$

wherein:
R$_1$ is PO(OR$_x$)$_2$, C$_1$-C$_6$ alkyl, C$_2$-C$_6$ alkenyl, C$_2$-C$_6$ alkynyl, C$_3$-C$_8$ cycloalkyl, 3 to 8-membered heterocyclyl, aryl, heteroaryl, CO(C$_1$-C$_6$ alkyl), CO(C$_2$-C$_6$ alkenyl), CO(C$_2$-C$_6$ alkynyl), CO(C$_3$-C$_8$ cycloalkyl), CO(3 to 8-membered heterocyclyl), CO(aryl), CO(heteroaryl), CON(R$_y$)$_2$, COO(C$_1$-C$_6$ alkyl), COO(C$_2$-C$_6$ alkenyl), COO(C$_2$-C$_6$ alkynyl), COO(C$_3$-C$_8$ cycloalkyl), COO(3 to 8-membered heterocyclyl), COO(aryl), or COO(heteroaryl), wherein each PO(OR$_x$)$_2$, C$_1$-C$_6$ alkyl, C$_2$-C$_6$ alkenyl, C$_2$-C$_6$ alkynyl, C$_3$-C$_8$ cycloalkyl, 3 to 8-membered heterocyclyl, aryl, heteroaryl, CO(C$_1$-C$_6$ alkyl), CO(C$_2$-C$_6$ alkenyl), CO(C$_2$-C$_6$ alkynyl), CO(C$_3$-C$_8$ cycloalkyl), CO(3 to 8-membered heterocyclyl), CO(aryl), CO(heteroaryl), CON(R$_y$)$_2$, COO(C$_1$-C$_6$ alkyl), COO(C$_2$-C$_6$ alkenyl), COO(C$_2$-C$_6$ alkynyl), COO(C$_3$-C$_8$ cycloalkyl), COO(3 to 8-membered heterocyclyl), COO(aryl) or COO(heteroaryl) is optionally substituted with one or more substituents selected from the group consisting of halogen, OH, NH$_2$, CN, C$_1$-C$_6$ alkyl, aryl, heteroaryl and C$_1$-C$_6$ alkoxy;

R$_2$, R$_3$, R$_4$, R$_5$ and R$_6$ are each independently H, PO(OR$_x$)$_2$, C$_1$-C$_6$ alkyl, C$_2$-C$_6$ alkenyl, C$_2$-C$_6$ alkynyl, C$_3$-C$_8$ cycloalkyl, 3 to 8-membered heterocyclyl, aryl, heteroaryl, CO(C$_1$-C$_6$ alkyl), CO(C$_2$-C$_6$ alkenyl), CO(C$_2$-C$_6$ alkynyl), CO(C$_3$-C$_8$ cycloalkyl), CO(3 to 8-membered heterocyclyl), CO(aryl), CO(heteroaryl), CON(R$_y$)$_2$, COO(C$_1$-C$_6$ alkyl), COO(C$_2$-C$_6$ alkenyl), COO(C$_2$-C$_6$ alkynyl), COO(C$_3$-C$_8$ cycloalkyl), COO(3 to 8-membered heterocyclyl), COO(aryl), COO(heteroaryl) wherein each PO(OR$_x$)$_2$, C$_1$-C$_6$ alkyl, C$_2$-C$_6$ alkenyl, C$_2$-C$_6$ alkynyl, C$_3$-C$_8$ cycloalkyl, 3 to 8-membered heterocyclyl, aryl, heteroaryl, CO(C$_1$-C$_6$ alkyl), CO(C$_2$-C$_6$ alkenyl), CO(C$_2$-C$_6$ alkynyl), CO(C$_3$-C$_8$ cycloalkyl), CO(3 to 8-membered heterocyclyl), CO(aryl), CO(heteroaryl), CON(R$_y$)$_2$, COO(C$_1$-C$_6$ alkyl), COO(C$_2$-C$_6$ alkenyl), COO(C$_2$-C$_6$ alkynyl), COO(C$_3$-C$_8$ cycloalkyl), COO(3 to 8-membered heterocyclyl), COO(aryl) or COO(heteroaryl) is optionally substituted with one or more substituents selected from the group consisting of halogen, OH, NH$_2$, CN, C$_1$-C$_6$ alkyl, aryl, heteroaryl and C$_1$-C$_6$ alkoxy.

3. The prodrug of claim 1, or a pharmaceutically acceptable salt, hydrate, solvate, or tautomer thereof, wherein the compound has the formula Ib:

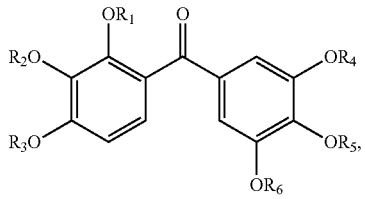

Ib wherein:
R$_1$ is H, PO(OR$_x$)$_2$, C$_2$-C$_6$ alkyl, C$_2$-C$_6$ alkenyl, C$_2$-C$_6$ alkynyl, C$_3$-C$_8$ cycloalkyl, 3 to 8-membered heterocyclyl, aryl, heteroaryl, CO(C$_1$-C$_6$ alkyl), CO(C$_2$-C$_6$ alkenyl), CO(C$_2$-C$_6$ alkynyl), CO(C$_3$-C$_8$ cycloalkyl), CO(3 to 8-membered heterocyclyl), CO(aryl), CO(heteroaryl), CON(R$_y$)$_2$, COO(C$_1$-C$_6$ alkyl), COO(C$_2$-C$_6$ alkenyl), COO(C$_2$-C$_6$ alkynyl), COO(C$_3$-C$_8$ cycloalkyl), COO(3 to 8-membered heterocyclyl), COO(aryl), or COO(heteroaryl), wherein each PO(OR$_x$)$_2$, C$_1$-C$_6$ alkyl, C$_2$-C$_6$ alkenyl, C$_2$-C$_6$ alkynyl, C$_3$-C$_8$ cycloalkyl, 3 to 8-membered heterocyclyl, aryl, heteroaryl, CO(C$_1$-C$_6$ alkyl), CO(C$_2$-C$_6$ alkenyl), CO(C$_2$-C$_6$ alkynyl), CO(C$_3$-C$_8$ cycloalkyl), CO(3 to 8-membered heterocyclyl), CO(aryl), CO(heteroaryl), CON(R$_y$)$_2$, COO(C$_1$-C$_6$ alkyl), COO(C$_2$-C$_6$ alkenyl), COO(C$_2$-C$_6$ alkynyl), COO(C$_3$-C$_8$ cycloalkyl), COO(3 to 8-membered heterocyclyl), COO(aryl) or COO(heteroaryl) is optionally substituted with one or more substituents selected from the group consisting of halogen, OH, NH$_2$, CN, C$_1$-C$_6$ alkyl, aryl, heteroaryl and C$_1$-C$_6$ alkoxy;

R$_2$, R$_3$, R$_4$, R$_5$ and R$_6$ are each independently H, PO(OR$_x$)$_2$, C$_1$-C$_6$ alkyl, C$_2$-C$_6$ alkenyl, C$_2$-C$_6$ alkynyl, C$_3$-C$_8$ cycloalkyl, 3 to 8-membered heterocyclyl, aryl, heteroaryl, CO(C$_1$-C$_6$ alkyl), CO(C$_2$-C$_6$ alkenyl), CO(C$_2$-C$_6$ alkynyl), CO(C$_3$-C$_8$ cycloalkyl), CO(3 to 8-membered heterocyclyl), CO(aryl), CO(heteroaryl), CON(R$_y$)$_2$, COO(C$_1$-C$_6$ alkyl), COO(C$_2$-C$_6$ alkenyl), COO(C$_2$-C$_6$ alkynyl), COO(C$_3$-C$_8$ cycloalkyl), COO(3 to 8-membered heterocyclyl), COO(aryl), or COO(heteroaryl), wherein each PO(OR$_x$)$_2$, C$_1$-C$_6$ alkyl, C$_2$-C$_6$ alkenyl, C$_2$-C$_6$ alkynyl, C$_3$-C$_8$ cycloalkyl, 3 to 8-membered heterocyclyl, aryl, heteroaryl, CO(C$_1$-C$_6$ alkyl), CO(C$_2$-C$_6$ alkenyl), CO(C$_2$-C$_6$ alkynyl), CO(C$_3$-C$_8$ cycloalkyl), CO(3 to 8-membered heterocyclyl), CO(aryl), CO(heteroaryl), CON(R$_y$)$_2$, COO(C$_1$-C$_6$ alkyl), COO(C$_2$-C$_6$ alkenyl), COO(C$_2$-C$_6$ alkynyl), COO(C$_3$-C$_8$ cycloalkyl), COO(3 to 8-membered heterocyclyl), COO(aryl) or COO(heteroaryl) is optionally substituted with one or more substituents selected from the group consisting of halogen, OH, NH$_2$, CN, C$_1$-C$_6$ alkyl, aryl, heteroaryl and C$_1$-C$_6$ alkoxy.

4. The prodrug of claim 1, or a pharmaceutically acceptable salt, hydrate, solvate, or tautomer thereof, wherein the compound has the formula Ic:

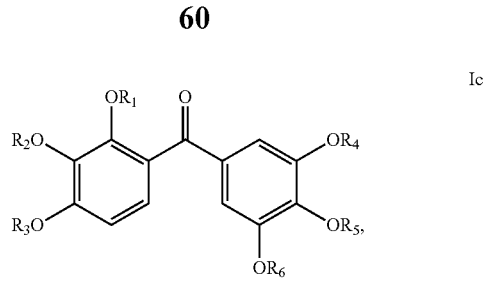

Ic wherein:
R$_1$, R$_2$, R$_3$, R$_4$, R$_5$ and R$_6$ are each independently PO(OR$_x$)$_2$, CO(C$_1$-C$_6$ alkyl), CO(C$_2$-C$_6$ alkenyl), CO(C$_2$-C$_6$ alkynyl), CO(C$_3$-C$_8$ cycloalkyl), CO(3 to 8-membered heterocyclyl), CO(aryl), CO(heteroaryl), CON(R$_y$)$_2$, COO(C$_1$-C$_6$ alkyl), COO(C$_2$-C$_6$ alkenyl), COO(C$_2$-C$_6$ alkynyl), COO(C$_3$-C$_8$ cycloalkyl), COO(3 to 8-membered heterocyclyl), or COO(aryl), COO(heteroaryl), wherein each PO(OR$_x$)$_2$, CO(C$_1$-C$_6$ alkyl), CO(C$_2$-C$_6$ alkenyl), CO(C$_2$-C$_6$ alkynyl), CO(C$_3$-C$_8$ cycloalkyl), CO(3 to 8-membered heterocyclyl), CO(aryl), CO(heteroaryl), CON(R$_y$)$_2$, COO(C$_1$-C$_6$ alkyl), COO(C$_2$-C$_6$ alkenyl), COO(C$_2$-C$_6$ alkynyl), COO(C$_3$-C$_8$ cycloalkyl), COO(3 to 8-membered heterocyclyl), COO(aryl) or COO(heteroaryl) is optionally substituted with one or more substituents selected from the group consisting of halogen, OH, NH$_2$, CN, C$_1$-C$_6$ alkyl, aryl, heteroaryl and C$_1$-C$_6$alkoxy.

5. The prodrug of claim 4, or a pharmaceutically acceptable salt, hydrate, solvate, or tautomer thereof, wherein the compound has the formula Id:

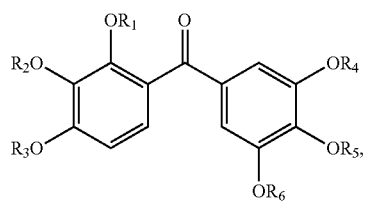

Id wherein:
R$_1$, R$_2$, R$_3$, R$_4$, R$_5$ and R$_6$ each are independently PO(OR$_x$)$_2$, CO(C$_1$-C$_6$ alkyl), CO(aryl), CO(heteroaryl), CON(R$_y$)$_2$, COO(C$_1$-C$_6$ alkyl), COO(aryl), COO(heteroaryl) wherein each PO(OR$_x$)$_2$, CO(C$_1$-C$_6$ alkyl), CO(aryl), CO(heteroaryl), CON(R$_y$)$_2$, COO(C$_1$-C$_6$ alkyl), COO(aryl), COO(heteroaryl) is optionally substituted with one or more substituents selected from the group consisting of halogen, OH, NH$_2$, CN, C$_1$-C$_6$ alkyl, aryl, heteroaryl and C$_1$-C$_6$ alkoxy.

6. The prodrug of claim 4, or a pharmaceutically acceptable salt, hydrate, solvate, or tautomer thereof, wherein the compound has a formula Id-1:

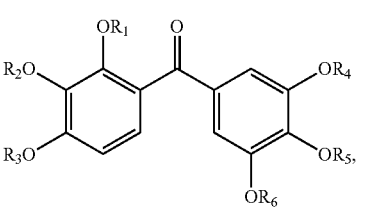

Id-1 wherein:

R$_1$, R$_2$, R$_3$, R$_4$, R$_5$ and R$_6$ are each independently CO(C$_1$-C$_6$ alkyl), CO(C$_3$-C$_6$ cycloalkyl), CO(C$_3$-C$_6$ heterocyclyl), CO(aryl), CO(heteroaryl), wherein each CO(C$_1$-C$_6$ alkyl), CO(C$_3$-C$_6$ cycloalkyl), CO(C$_3$-C$_6$ heterocycle), CO(aryl) or CO(heteroaryl) is optionally substituted with one or more substituents selected from the group consisting of halogen, OH, NH$_2$, CN, C$_1$-C$_6$ alkyl, aryl, heteroaryl and C$_1$-C$_6$ alkoxy.

7. The prodrug of claim 1, or a pharmaceutically acceptable salt, hydrate, solvate, or tautomer thereof, wherein the compound has a formula Ie:

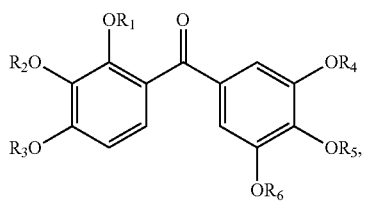

wherein:

R$_1$, R$_2$, R$_3$, R$_4$, R$_5$ and R$_6$ are each independently CO(C$_1$-C$_3$ alkyl), wherein CO(C$_1$-C$_3$ alkyl) is optionally substituted with one or more substituents selected from the group consisting of halogen, OH, NH$_2$, CN, C$_1$-C$_6$ alkyl, aryl, heteroaryl and C$_1$-C$_6$ alkoxy.

8. The prodrug of claim 7, or a pharmaceutically acceptable salt, hydrate, solvate, or tautomer thereof, wherein each of R$_1$, R$_2$, R$_3$, R$_4$, R$_5$ and R$_6$ is CO(C$_1$-C$_2$ alkyl).

9. The prodrug of claim 1, or a pharmaceutically acceptable salt, hydrate, solvate, or tautomer thereof, wherein the compound is selected from the group consisting of:

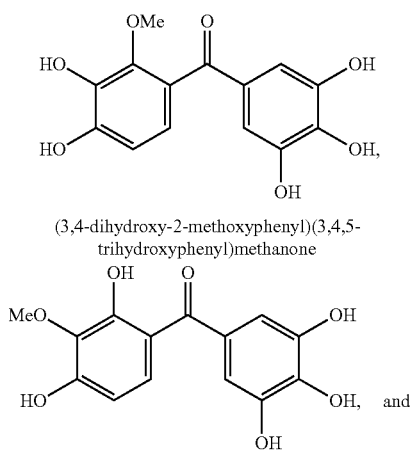

(3,4-dihydroxy-2-methoxyphenyl)(3,4,5-trihydroxyphenyl)methanone (2,4-dihydroxy-2-methoxyphenyl)(3,4,5-trihydroxyphenyl)methanone (3,4-dihydroxy-5-methoxyphenyl)(2,3,4-trihydroxyphenyl)methanone 10. A pharmaceutical composition comprising the prodrug of claim 1, or a pharmaceutically acceptable salt, hydrate, solvate, or tautomer thereof, and a pharmaceutically acceptable carrier.

11. A method of treating a disease associated with a deficiency in HDAC1 deacetylase activity comprising administering to a patient in need thereof an effective amount of a prodrug of claim 1, or a pharmaceutically acceptable salt, hydrate, solvate, or tautomer thereof.

12. The method of claim 11, wherein the compound activates HDAC1 deacetylase activity.

13. The method of claim 11, wherein the compound increases the expression of genes involved in cytokine responses, neurogenesis, and/or central nervous system development.

14. The method of claim 13, wherein the genes involved in cytokine responses are genes involved in interferon (IFN)-γ and/or IFN-β responses.

15. The method of claim 11, wherein the disease is a neurodegenerative disease, neurological disorder, psychiatric disorder, or cognitive deficit.

16. The method of claim 11, wherein the disease is a dementia or amyotrophic lateral sclerosis (ALS).

17. The method of claim 16, wherein the dementia is Alzheimer's disease, frontotemporal dementia, or Parkinson's disease.

18. The method of claim 11, wherein the disease is major depression, bipolar disorder, and schizophrenia.

19. The method of claim 11, wherein administering is performed orally, parenterally, intranasally, subcutaneously, by injection, or by infusion.

20. The method of claim 11, wherein the prodrug of claim 1 is a prodrug of the compound Ih:

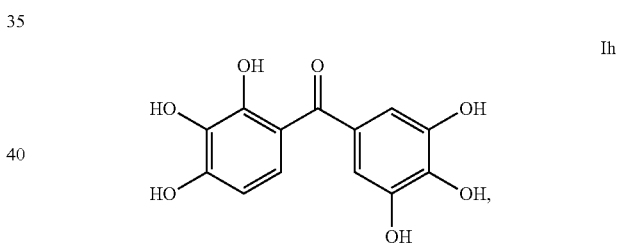

or a pharmaceutically acceptable salt, hydrate, solvate, or tautomer thereof.

21. A method of activating HDAC1 activity comprising contacting a cell with a prodrug of claim 1, or a pharmaceutically acceptable salt, hydrate, solvate, or tautomer thereof.

22. A prodrug of a compound of Formula II:

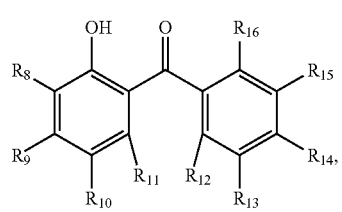

or a pharmaceutically acceptable salt, hydrate, solvate, or tautomer thereof, wherein:

each R$_7$, R$_8$, R$_9$, R$_{10}$, R$_{11}$, R$_{12}$, R$_{13}$, R$_{14}$, R$_{15}$ and R$_{16}$ is independently H, OH or halogen provided that any two of $R_7$, $R_8$, $R_9$, $R_{10}$ and $R_{11}$ and any two of $R_{12}$, $R_{13}$, $R_{14}$, $R_{15}$ and $R_{16}$ are 2 adjacent OH groups and that (2) the prodrug is not:
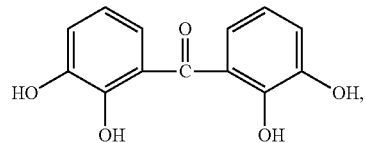
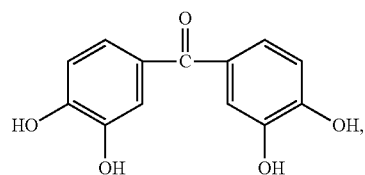
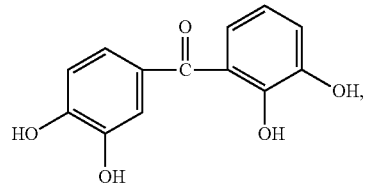
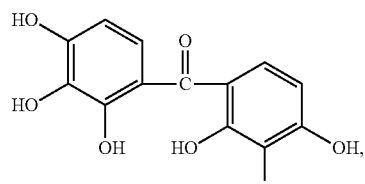
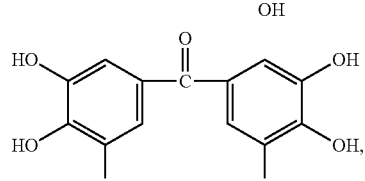
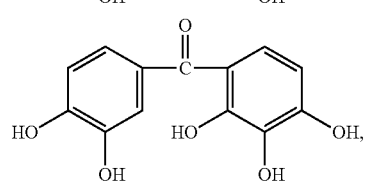
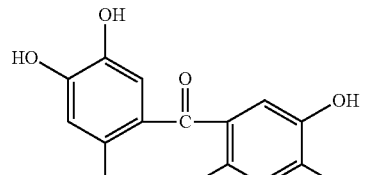
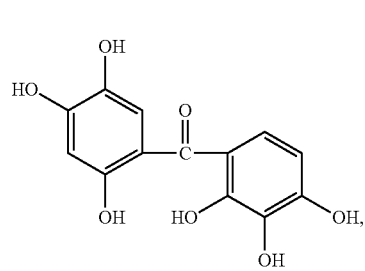
-continued
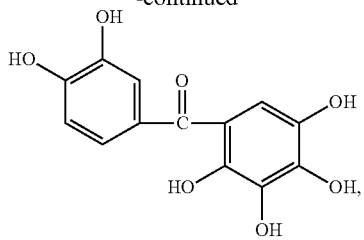
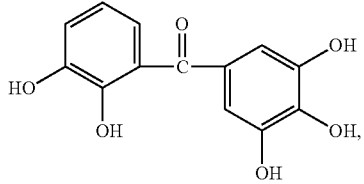
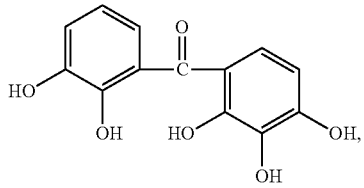
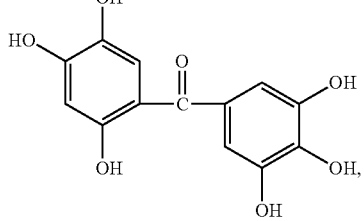
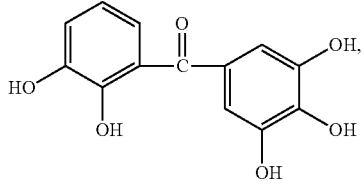
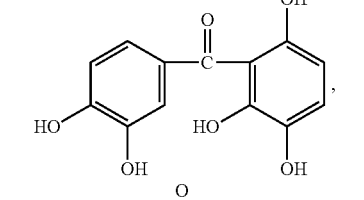
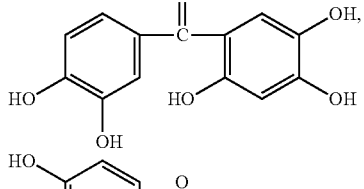
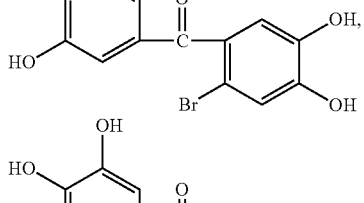
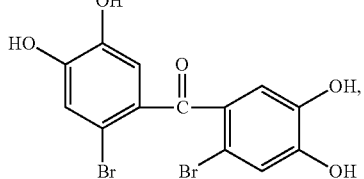

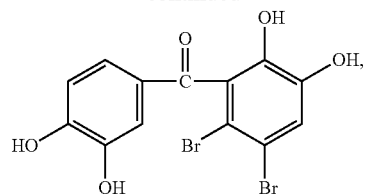
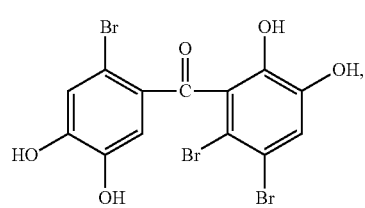
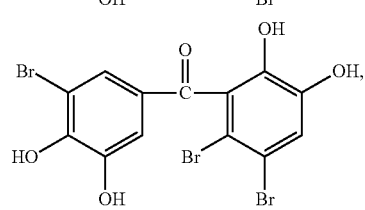
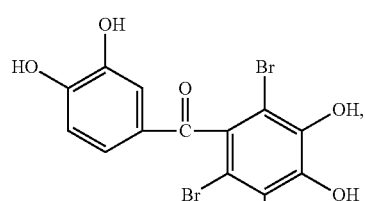
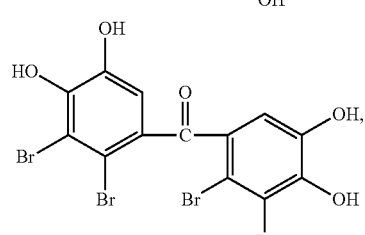
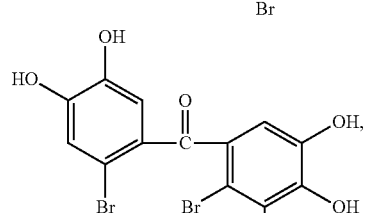
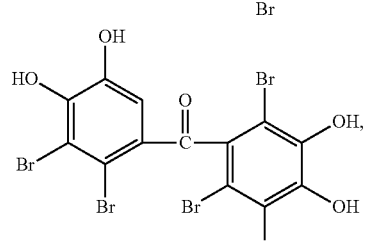
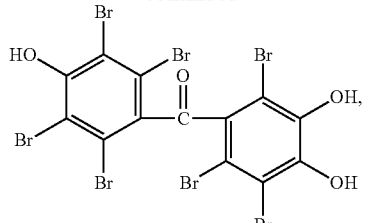
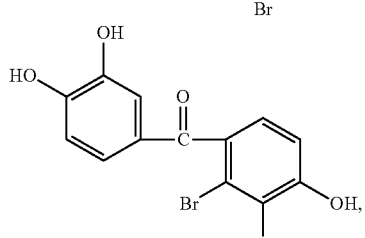
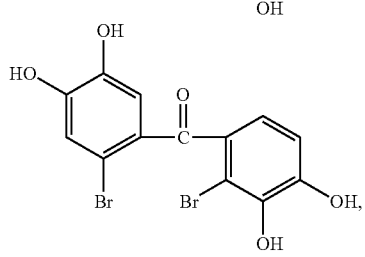
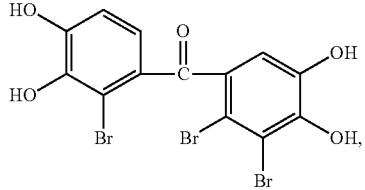
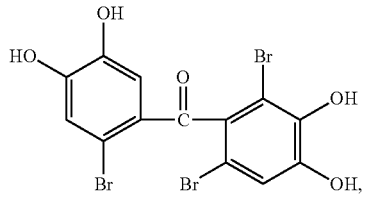
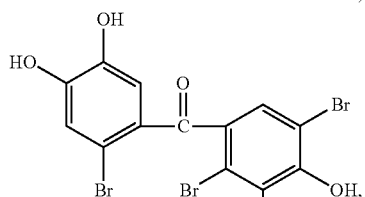
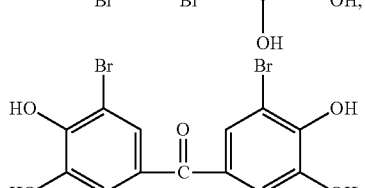
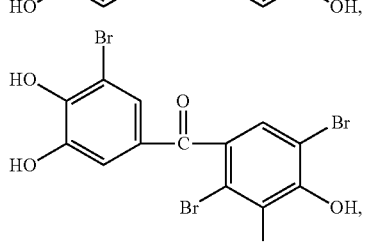

-continued

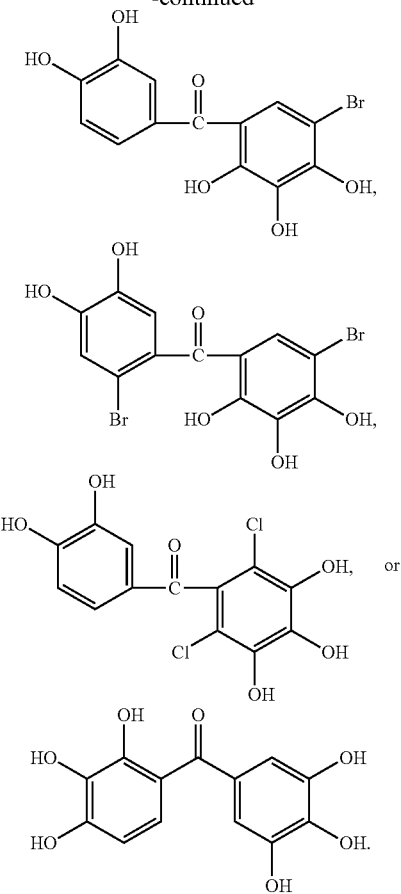

23. The prodrug of claim 22, a pharmaceutically acceptable salt, hydrate, solvate, or tautomer thereof, wherein the compound has the Formula IIa:

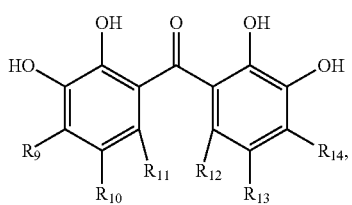

wherein $R_9$, $R_{10}$, $R_{11}$, $R_{12}$, $R_{13}$ and $R_{14}$, are each independently H, OH or halogen.

24. The prodrug of claim 22, or a pharmaceutically acceptable salt, hydrate, solvate, or tautomer thereof, wherein the compound has a Formula IIb:

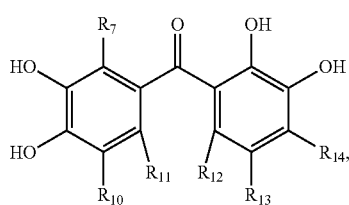

wherein $R_7$, $R_{10}$, $R_{11}$, $R_{12}$, $R_{13}$ and $R_{14}$ are each independently H, OH or halogen.

25. The prodrug of claim 22, or a pharmaceutically acceptable salt, hydrate, solvate, or tautomer thereof, wherein the compound has a Formula IIc:

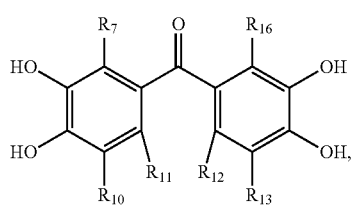

wherein $R_7$, $R_{10}$, $R_{11}$, $R_{12}$, $R_{13}$ and $R_{16}$ are each independently H, OH or halogen.

26. The prodrug of claim 22, or a pharmaceutically acceptable salt, hydrate, solvate, or tautomer thereof, wherein the compound is II-1:

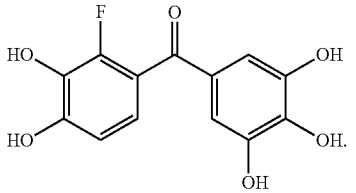

27. The prodrug of claim 22, or a pharmaceutically acceptable salt, hydrate, solvate, or tautomer thereof, wherein the compound is selected from the group consisting of:

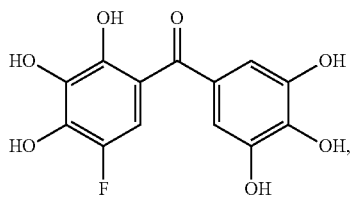

(5-fluoro-2,3,4-trihydroxyphenyl)(3,4,5-trihydroxyphenyl)methanone

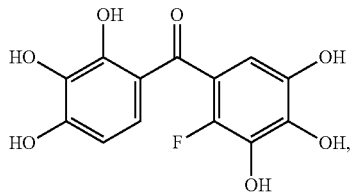

(2-fluoro-3,4,5-trihydroxyphenyl)(2,3,4-trihydroxyphenyl)methanone

-continued

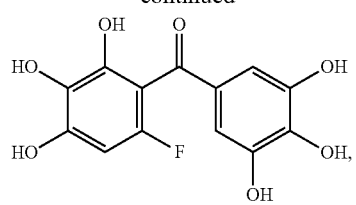

(6-fluoro-2,3,4-trihydroxyphenyl)
(3,4,5-trihydroxyphenyl)methanone

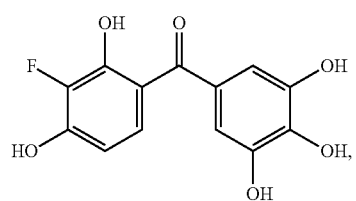

(3-fluoro-2,4-dihydroxyphenyl)
(3,4,5-trihydroxyphenyl)methanone

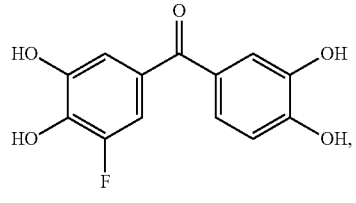

(3,4-dihydroxyphenyl)(3-fluoro-
4,5-dihydroxyphenyl)methanone

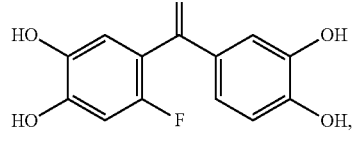

(3,4-dihydroxyphenyl)(2-fluoro-
4,5-dihydroxyphenyl)methanone

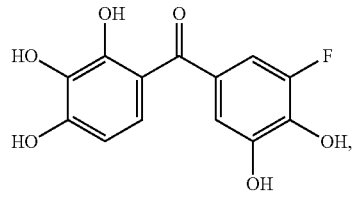

(3-fluoro-4,5-dihydroxyphenyl)
(2,3,4-trihydroxyphenyl)methanone

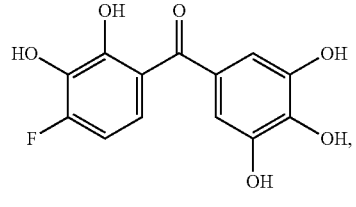

(4-fluoro-2,3-dihydroxyphenyl)
(3,4,5-trihydroxyphenyl)methanone

-continued

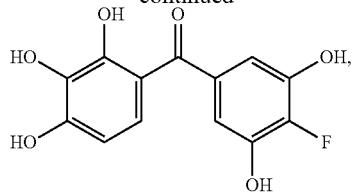

(4-fluoro-3,5-dihydroxyphenyl)
(2,3,4-trihydroxyphenyl)methanone

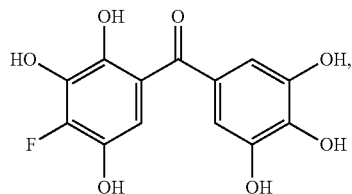

(4-fluoro-2,3,5-trihydroxyphenyl)
(3,4,5-trihydroxyphenyl)methanone

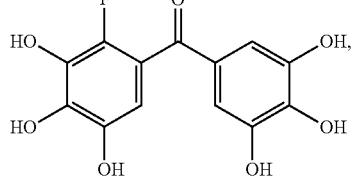

(2-fluoro-3,4,5-trihydroxyphenyl)
(3,4,5-trihydroxyphenyl)methanone

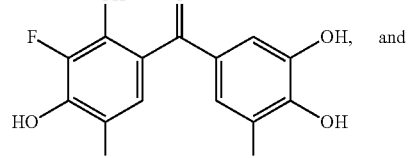

(3-fluoro-2,4,5-trihydroxyphenyl)
(3,4,5-trihydroxyphenyl)methanone

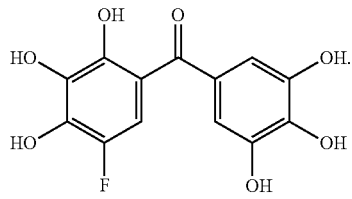

(5-fluoro-2,3,5-trihydroxyphenyl)
(3,4,5-trihydroxyphenyl)methanone

28. A pharmaceutical composition comprising the prodrug according to claim 22, or a pharmaceutically acceptable salt, hydrate, solvate, or tautomer thereof, and a pharmaceutically acceptable carrier.

29. A method of treating a disease associated with a deficiency in HDAC1 deacetylase activity comprising administering to a patient in need thereof a prodrug of claim 22, or a pharmaceutically acceptable salt, hydrate, solvate, or tautomer thereof.

30. The method of claim 29, wherein the compound activates HDAC1 deacetylase activity.

31. The method of claim 29, wherein the compound increases the expression of genes involved in cytokine responses, neurogenesis, and/or central nervous system development.

32. The method of claim 31, wherein the genes involved in cytokine responses are genes involved in interferon (IFN)-γ and/or IFN-β responses.

33. The method of claim 29, wherein the disease is a neurodegenerative disease, neurological disorder, psychiatric disorder, or cognitive deficit.

34. The method of claim 29, wherein the disease is dementia or amyotrophic lateral sclerosis (ALS).

35. The method of claim 34, wherein the dementia is Alzheimer's disease, frontotemporal dementia, or Parkinson's disease.

36. The method of claim 29, wherein the disease is major depression, bipolar disorder, and schizophrenia.

37. The method of claim 29, wherein administering is performed orally, parenterally, intranasally, subcutaneously, by injection or by infusion.

38. The method of claim 29, wherein the prodrug is a prodrug of the compound IId:

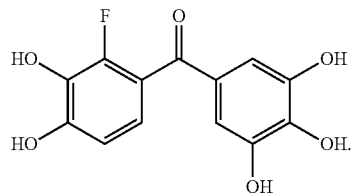

39. A method of activating HDAC1 activity comprising contacting a cell with a prodrug of claim 22, or a pharmaceutically acceptable salt, hydrate, solvate, or tautomer thereof.

40. A kit comprising one or more prodrugs of claim 1, or a pharmaceutically acceptable salt, hydrate, solvate, or tautomer thereof.

41. The kit of claim 40, further comprising a compound effective in treating a disease responsive to HDAC1 activation.

42. The kit of claim 41, wherein the compound effective in treating a disease responsive to HDAC1 activation is selected from the group comprising Aricept® (donepezil), Exelon® (rivastigmine), Razadyne® (galantamine), Cognex® (tacrine), and Namenda® (memantine).

* * * * *

UNITED STATES PATENT AND TRADEMARK OFFICE
CERTIFICATE OF CORRECTION

PATENT NO. : 11,639,325 B2  
APPLICATION NO. : 17/116427  
DATED : May 2, 2023  
INVENTOR(S) : Li-Huei Tsai et al.

Page 1 of 2

It is certified that error appears in the above-identified patent and that said Letters Patent is hereby corrected as shown below:

In the Claims

In Claim 22, in Column 64, Line 10, the formula: 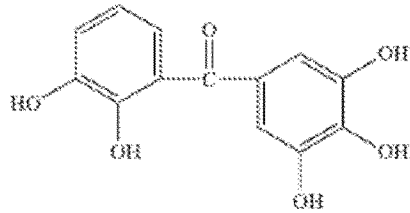 should be replaced with the formula: 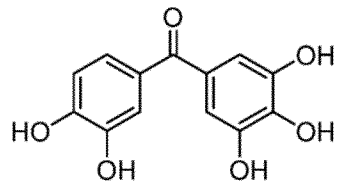 .

In Claim 22, in Column 66, Line 5, the formula: 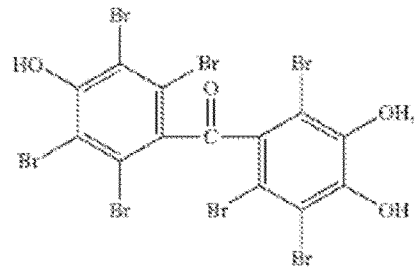 should be replaced with the formula:  .

Signed and Sealed this  
Eighth Day of October, 2024

Katherine Kelly Vidal  
*Director of the United States Patent and Trademark Office*

CERTIFICATE OF CORRECTION (continued)
U.S. Pat. No. 11,639,325 B2

In Claim 22, in Column 66, Line 60, the formula: 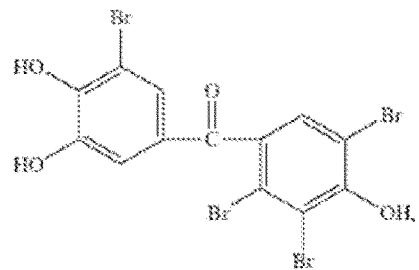 should be replaced with the formula: 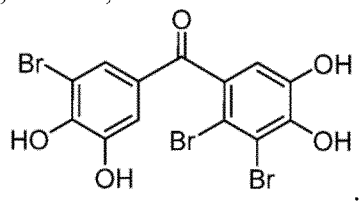 .

In Claim 23, in Column 67, Lines 37-38:
"The prodrug of claim 22, a pharmaceutically acceptable salt"
Should read:
--The prodrug of claim 22, or a pharmaceutically acceptable salt--.